US012597525B2

(12) United States Patent
Kleinloog et al.

(10) Patent No.: US 12,597,525 B2
(45) Date of Patent: Apr. 7, 2026

(54) HEALTHCARE SYSTEM FOR PROVIDING MEDICAL INSIGHTS

(71) Applicant: Roche Diagnostics Operations, Inc., Indianapolis, IN (US)

(72) Inventors: Arnoud Kleinloog, Rotkreuz (CH); Philippe Kraeuchi, Maennedorf (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 320 days.

(21) Appl. No.: 18/066,045

(22) Filed: Dec. 14, 2022

(65) Prior Publication Data

US 2023/0197288 A1 Jun. 22, 2023

(30) Foreign Application Priority Data

Dec. 17, 2021 (EP) ..................................... 21215530

(51) Int. Cl.
| | |
|---|---|
| *G16H 50/70* | (2018.01) |
| *G06F 21/60* | (2013.01) |
| *G06F 21/62* | (2013.01) |
| *G16H 10/60* | (2018.01) |

(52) U.S. Cl.
CPC ........... *G16H 50/70* (2018.01); *G06F 21/602* (2013.01); *G06F 21/6245* (2013.01); *G16H 10/60* (2018.01)

(58) Field of Classification Search
CPC ...... G16H 50/70; G16H 10/60; G06F 21/602; G06F 21/6245
USPC ....................................................... 705/2–3
See application file for complete search history.

(56) References Cited

U.S. PATENT DOCUMENTS

| | | | |
|---|---|---|---|
| 2004/0078430 A1* | 4/2004 | Aubert ................... | G06Q 10/06 709/204 |
| 2014/0090063 A1* | 3/2014 | Calnan ...................... | G06F 8/71 726/25 |
| 2016/0147954 A1* | 5/2016 | Ng Tari .................. | G16H 40/20 705/3 |
| 2019/0156947 A1* | 5/2019 | Nakamura ............. | G16H 50/20 |
| 2021/0174941 A1 | 6/2021 | Mathur et al. | |

FOREIGN PATENT DOCUMENTS

EP 2953053 B1 * 2/2019 ............. G16H 10/60

OTHER PUBLICATIONS

Anonymous, Architecting for HIPAA Security and Compliance on Amazon Web Services, AWS Whitepaper, 2021, 54 pp.
(Continued)

*Primary Examiner* — Kambiz Abdi
*Assistant Examiner* — Sheryl G Patel
(74) *Attorney, Agent, or Firm* — Lee & Hayes, P.C.

(57) ABSTRACT

A healthcare system for providing medical insights by receiving medically relevant data (MRD) and providing results of medical algorithms using the medically relevant data (MRD), the medically relevant data (MRD) comprising quantitative medical data created based on at least one diagnostic measurement method, wherein the healthcare system comprises two or more medical algorithm modules and a service module, and the functionalities are separated between the medical algorithm modules and the service module.

20 Claims, 7 Drawing Sheets

(56) References Cited

OTHER PUBLICATIONS

Anonymous, Documentation Kubernetes-Concepts, 2020, retrieved from https://github.com/dohsimpson/kubernetes-doc-pdf/raw/a5a0a15050249de56fcadd332840dd5932219ad9/PDFs/Concepts.pdf.

Anonymous, HIPPA Compliance with Kubernetes: The Privacy Rule, The Elastisys Tech Blog (/blog/), 2020, retrieved from https://elastisys.com/category/compliance/healthcare, 7 pp.

Anonymous, HIPPA Security Series Security 101 for Covered Entities, Department of Health Human Services USA, Centers for Medicare &amp; Medicaid Services, 2007, 11 pp., vol. 2, Paper 1.

European Search Report issued Jun. 23, 2022, in Application No. 21215530.3, 3 pp.

Rouzbeh, Fatemeh et al., Collaborative Cloud Computing Framework for Health Data with Open Source Technologies, Proceedings of the 11th ACM International Conference on Bioinformatics, Computational Biology and Health Informatics, 2020, 4 pp., Article No. 48, Abstract.

Vitabile, Salvatore et al., Medical Data Processing and Analysis for Remote Health and Activities Monitoring, High-Performance Modelling and Simulation for Big Data Applications Selected Results of the COST Action IC1406 cHiPSet, 2019, pp. 186-220, 11400, Joanna Kolodziej and Horacio Gonzalez-Velez, Eds.

European Office Action (Communication pursuant to Article 94(3) EPC) issued in EP Application No. 22213844.8, dated Sep. 2, 2025; 18 pages.

Souppaya, et al., "Application Container Security Guide", National Institute of Standards and Technology, Apr. 10, 2017, pp. 1-57, XP093301277, DOI: 10.6028/NIST.SP.800-190; retrieved from the Internet: <https://csrn.nist.gov/csrc/media/publications/sp/800-190/draft/documents/sp800-190-draft.pdf>, retrieved on Jul. 31, 2025.

* cited by examiner

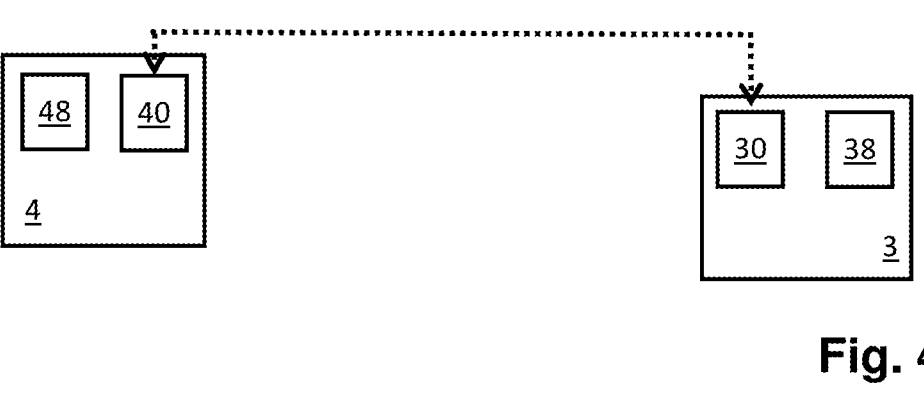
Fig. 4a
Fig. 4b
Fig. 4c
Fig. 4d

100

100

HEALTHCARE SYSTEM FOR PROVIDING MEDICAL INSIGHTS

CROSS-REFERENCE TO RELATED APPLICATIONS

This application claims priority to European Patent Application No. 21215530.3, filed Dec. 17, 2021, the disclosure of which is hereby incorporated by reference in its entirety.

TECHNICAL FIELD

The invention relates to the field of healthcare systems for providing medical insights.

BACKGROUND

Medical algorithms allow to combine and analyze medically relevant data, in particular quantitative medical data created based on at least one diagnostic measurement method, and the results of medical algorithms allow for supporting medical decision making and/or guiding medical workflows. The medical insights provided by the medical algorithms can allow for significant improvements in patient care and medical outcomes. It is thus advantageous to provide a healthcare system that can allow for a secure use of medical algorithms.

SUMMARY

It is the purpose of this invention to provide systems, combinations, modules, methods, and devices that expand the current state of the art. For this purpose, systems, combinations, modules, methods, and devices according to the independent claims are proposed and particular embodiments of the invention are set out in the dependent claims.

A healthcare system (e.g., a healthcare data processing system) for providing medical insights or medical data processing results by receiving medically relevant data or medical records and providing results of medical algorithms applied to the medically relevant data, the medically relevant data or medical records data (MRD) comprising quantitative medical data created based on at least one diagnostic measurement method, is proposed, wherein the healthcare system comprises two or more medical algorithm modules and a service module;
wherein the medical algorithm modules
each comprises a medical algorithm, the medical algorithm being programmed for algorithmically creating results using the medically relevant data,
each is hosted in an isolated runtime environment for its medical algorithm,
each comprises a medical algorithm application programing interface, the medical algorithm application programing interface being programmed for allowing
to receive medically relevant data from outside the medical algorithm module and provide (e.g., transmit) the medically relevant data or records to the medical algorithm of the medical algorithm module, and
to provide (e.g., transmit) results from the medical algorithm to outside of the medical algorithm module (e.g., an external application);
wherein the service module comprises a service application programing interface, the service application programing interface being designed for interacting with the medical algorithm application programing interfaces for allowing
to provide medically relevant data or records data to the medical algorithm modules, and
to receive results of medical algorithms from the medical algorithm modules,
the service application programing interface being programmed for interacting with (one or more) integration module(s) for allowing
to receive medically relevant data from (the one or more) integration module(s),
to provide results of medical algorithms to (the one or more) integration module(s), and
to receive service (e.g., operational) data from (the one or more) integration module(s), wherein the service/operational data may relate
to the operation and use of the medical algorithm module(s); and
wherein the service module comprises
an encryption module designed for decrypting and/or encrypting data,
a security module designed for monitoring possible security risks for the medical algorithms,
an authorization module designed for authorizing, using received service data, the use of at least one of the medical algorithms, and
an activity tracking module designed for recording at least some activities in the context of the medical algorithms.

According to some embodiments, the isolated runtime environment is based on an immutable medical algorithm container image.

According to some embodiments, the medical algorithms of the two or more medical algorithm modules of the healthcare system are programmed for processing quantitative medical data.

According to some embodiments, none of the medical algorithm modules comprises an encryption/decryption functionality, a security functionality, an authorization functionality, or an activity tracking functionality or is otherwise restricted from implementing such functionality.

According to some embodiments, each of the medical algorithm modules comprises a medical algorithm graphical user interface, the medical algorithm graphical user interface being designed for allowing
a user to input medically relevant data to the medical algorithm module and to provide the medically relevant data to the medical algorithm of the medical algorithm module, and
to display results from the medical algorithm.

According to some embodiments, each of the medical algorithm modules comprises an input validation module designed for validating the medically relevant data provided to the medical algorithm module and for providing medically relevant data to the medical algorithm only in case the medically relevant data is validated.

According to some embodiments, each of the medical algorithm application programing interfaces comprises one or more of the following interface modules:
a labelling information module programmed for providing labelling information;
a meta module programmed for providing information on a structured definition of the medical algorithm and its input and output;

a ready module programmed for providing information to indicate that the medical algorithm of the medical algorithm module is ready to serve requests; and an alive module programmed for providing information to indicate that the medical algorithm of the medical algorithm module is running.

According to some embodiments, the service module comprises at least one additional service sub-module(s), the at least one additional service sub-module(s) being one or more of the following:

a medical algorithm catalogue database programmed for providing information related to the medical algorithms available via the healthcare system;

a medical algorithm search module programmed for searching the medical algorithms available via the healthcare system;

a product labelling information module programmed for providing product labelling information on and/or by the respective manufacturer of the medical algorithms available via the healthcare system;

a user management module programmed for managing user access to the medical algorithms available via the healthcare system;

a billing module programmed for managing billing information on the use of at least one of the medical algorithms available via the healthcare system;

a subscription module programmed for managing subscriptions for using at least one of the medical algorithms available via the healthcare system;

a usage statistics module programmed for providing usage statistics;

a resource management module programmed for allocating computing and/or networking resources to the components of the healthcare system;

a resource monitoring module programmed for monitoring computing and/or networking resources within the healthcare system;

a usage prediction module programmed for predicting the upcoming usage of medical algorithm modules and for starting and/or terminating medical algorithm modules according to the prediction of the upcoming usage;

a generic input validation module programmed for a generic validation of the medically relevant data provided to the healthcare system;

a data transformation module programmed for transforming data, e.g. for transforming medically relevant data prior to providing the medically relevant data to a medical algorithm module and/or for transforming a result of a medical algorithm prior to providing the result to an integration module;

a signing module programmed for (digitally) signing at least some of the results of the medical algorithms; and a data associating module programmed for associating data, e.g. for associating data relating to a same patient.

According to some embodiments, the service module is programmed for processing the medically relevant data and the results of the medical algorithms without adding medical value to the medically relevant data or the results.

According to some embodiments, the service application programing interface is further programmed for interacting with one or more integration module(s) for allowing to provide service data (or operational data) to the one or more integration module(s).

According to some embodiments, the healthcare system is designed such that the isolated runtime environment of a medical algorithm module cannot directly access the computing and/or network resources of an isolated runtime environment of any other medical algorithm module. According to some specific embodiments, the healthcare system is further designed such that the isolated runtime environment of a medical algorithm module cannot directly access the computing and/or network resources of an isolated runtime environment of the service module or any component thereof.

According to some embodiments, the healthcare system is designed such that the medical algorithm modules can communicate with each other via the service module.

According to some embodiments, the healthcare system comprises at least one medical algorithm adapter designed for connecting with an external medical algorithm comprised in an external application, the medical algorithm adapter comprising an adapter application programing interface designed for allowing to receive medically relevant data from the service module, to provide medically relevant data to the external application, to receive results of the external medical algorithm from the external application, and to provide results of the external medical algorithm to the service module.

A healthcare system combination of one of the proposed healthcare systems and an integration module is proposed, wherein the integration module comprises an integration module interface designed for providing medically relevant data to the healthcare system, receiving results of medical algorithms from the healthcare system, providing service data to the healthcare system.

According to some embodiments, the integration module comprises a portal.

According to some embodiments, the healthcare system and the integration module are in a shared protected network.

According to some embodiments, the healthcare system is in a first protected network and the integration module is in a second protected network.

According to some embodiments, the integration module interface comprises an integration application programing interface designed for interacting with the service application programing interface for allowing to provide medically relevant data and service data from the integration module to the service module, and to receive results of medical algorithms from the service module to the integration module.

According to some embodiments, the integration module interface comprises an integration graphical user interface designed for allowing a user to input and receive data for allowing a user to input an order (e.g., a request) for a result of a medical algorithm of the healthcare system, and to display results from the medical algorithm to a user.

According to some specific embodiments, the integration graphical user interface comprises a dashboard designed for displaying information related to the medical algorithms.

According to some embodiments, the integration module interface is further designed for receiving service data from the healthcare system.

According to some embodiments, the integration module comprises, is comprised in, and/or is connected to a laboratory information system (LIS), a hospital information system (HIS), a laboratory middleware, a hospital middleware, and/or an electronic medical record (EMR).

Proposed is a medical algorithm module designed as one of the two or more medical algorithm modules of one of the proposed healthcare systems resp. one of the proposed healthcare system combinations.

Proposed is a method for operating one of the proposed healthcare systems, the method comprising the steps of:

receiving, by the service application programing interface, encrypted medically relevant data and service data, the service data comprising an indication that a result of a medical algorithm of the healthcare system based on the medically relevant data is ordered, this medical algorithm being the referred to as the ordered (e.g., requested) medical algorithm;

decrypting, by the encryption module, the received encrypted medically relevant data;

monitoring, by the security module, possible security risks at least for the ordered medical algorithm;

authorizing, by the authorization module and using the received service data, the use of the ordered medical algorithm;

providing, by the service application programing interface to the medical algorithm application programing interface of at least one medical algorithm module comprising the ordered medical algorithm, this medical algorithm module being referred to as the chosen medical algorithm module, the received medically relevant data;

providing, by the medical algorithm application programing interface of the chosen medical algorithm module to the medical algorithm of the chosen medical algorithm module, the received medically relevant data;

algorithmically creating, by the ordered medical algorithm of the chosen medical algorithm module and using the received medically relevant data, a result, this result being referred to as the ordered result;

providing, by the ordered medical algorithm of the chosen medical algorithm module to the medical algorithm application programing interface of the chosen medical algorithm module, the ordered result;

providing, by the medical algorithm application programing interface of the chosen medical algorithm module to the service application programing interface, the ordered result;

recording, by the activity tracking module, at least some activities in the context of the ordered medical algorithm.

According to some variants, the method further comprising the steps of:

encrypting, by the encryption module, the ordered result; and providing, to an integration module, the encrypted ordered result.

Proposed is a computer-readable storage medium comprising instructions which, when executed, causes the computer to carry out the method of one of the proposed methods for operating the healthcare system.

BRIEF DESCRIPTION OF THE DRAWINGS

Specific embodiments of the invention are described in the following with reference to the drawings, which are for the purpose of illustrating the present specific embodiments of the inventions and not for limiting the same. In the drawings.

FIGS. 4a-4d shows multiple variants of direct interactions between an integration module and a medical algorithm module;

DETAILED DESCRIPTION

Figure 1:
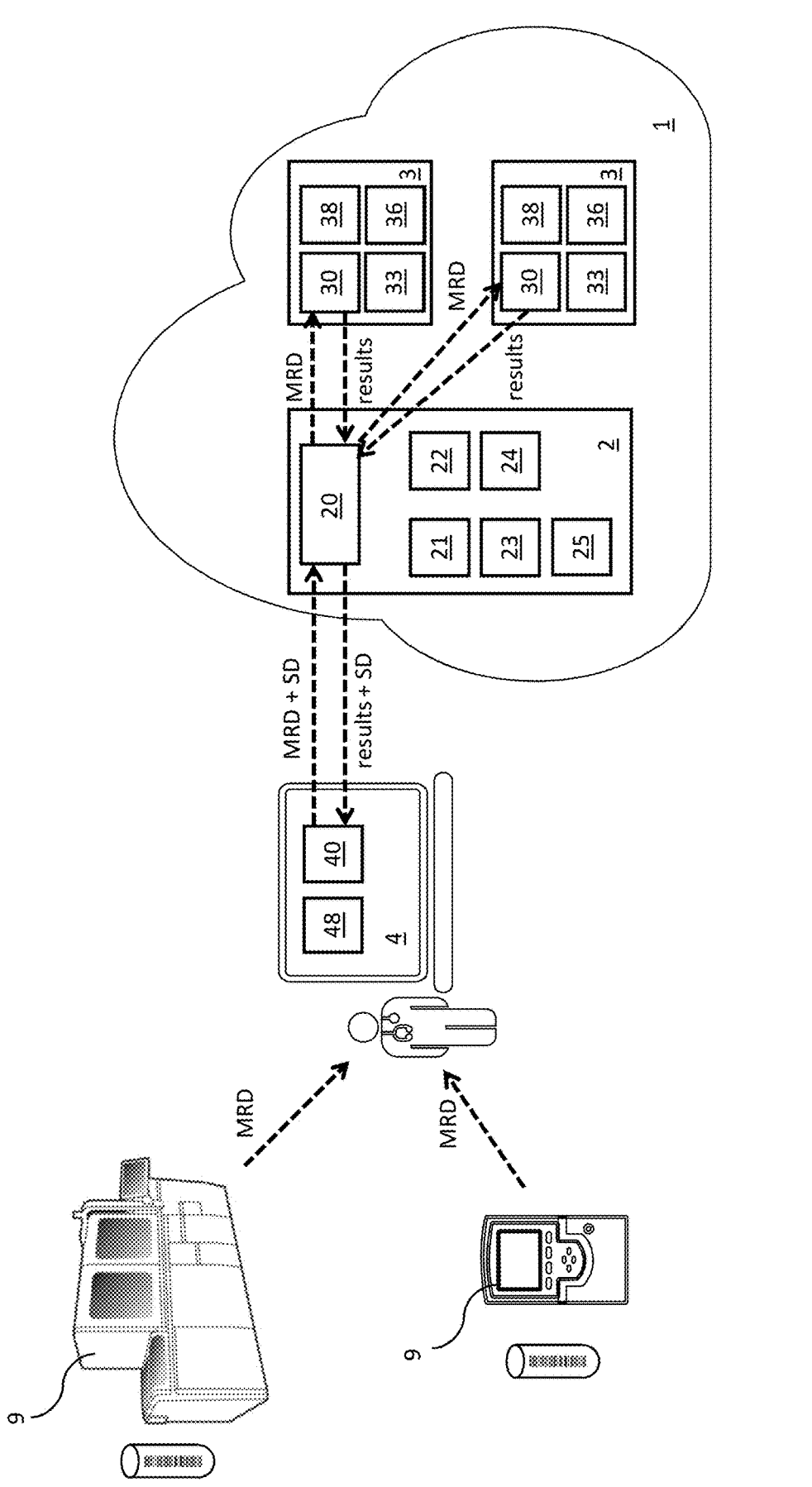
FIG. 1 shows a healthcare system and systems connected thereto.

A healthcare system 1 for receiving medically relevant data or medical records data, MRD, and providing results of medical algorithms applied to the MRD, which can e.g. allow the healthcare system 1 to provide medical insights, is proposed.

The medically relevant data MRD comprises quantitative medical data created based on at least one diagnostic measurement method, e.g. an in-vitro diagnostic ("IVD") measurement method (e.g. performed on a sample by using an IVD laboratory instrument and/or an IVD point-of-care instrument) and/or using an in-vivo measurement method (e.g. performed on a patient by using a thermometer and/or a blood pressure monitor). According to some embodiments, the medically relevant data MRD in addition comprises qualitative medical data, e.g. a qualitative assessment by a physician (e.g. that a certain symptom is present in a patient, such as a rash or a coughing). According to some embodiments, the medically relevant data MRD comprises data concerning a patient, e.g. data concerning the patient's medical history (e.g. earlier diagnosis), data concerning the patient's medication history, data concerning the patient's family medical history, data on the patient's lifestyle (e.g. smoker(non-smoker), and/or data concerning the patient's demographics (e.g. gender, age). Quantitative medically relevant data MRD can be in the form of values or ranges.

The proposed healthcare system 1 comprises two or more medical algorithm modules 3.

Each of the medical algorithm modules 3 comprises a medical algorithm 33 that is designed for algorithmically creating results using medically relevant data MRD, e.g. wherein the medical algorithm 33 outputs an identical result when using identical medically relevant data MRD as an input. The medical algorithm 33 may comprise several sub-algorithms. The medical algorithm 33 may be designed to execute a plurality of computations. The result can e.g. be a numeric value (e.g. "80 mg/cm3"), a range (e.g. "80-120 mg/cm3""), a qualitative indication (e.g. "yes" or "no"), and/or a text. According to an example, the result is a numeric value and a text, wherein the content of text depends on the numeric value, e.g. indicating a guidance information (e.g. a treatment recommendation) based on the numeric value.

According to some embodiments, the healthcare system 1 comprises at least two medical algorithm modules 3 that each comprises a medical algorithm 33 that requires medically relevant data MRD comprising quantitative medical data created using at least one diagnostic measurement method. According to some specific embodiments, the healthcare system 1 can in addition comprise a medical algorithm module 3 that comprises a medical algorithm 33 that does not require medically relevant data MRD comprising quantitative medical data created using at least one diagnostic measurement method, e.g. wherein the medical algorithm 33 only requires qualitative medical data.

Each of the medical algorithm module 3 is hosted in, e.g. comprised in, an isolated runtime environment for its medical algorithm 33.

According to some embodiments, the isolated runtime environment comprises a container (instance) based on an immutable medical algorithm container image. Using an immutable medical algorithm container image can allow for creating the same well-defined medical algorithm module 3 every time an instance of the medical algorithm module 3 is created; this can allow increasing the probability that the medical algorithm 33 works as intended, which is of increased importance since the results of the medical algorithm modules 3 can have a decisive influence on a patient future medical treatment. The healthcare system 1 can comprise multiple medical algorithm modules 3 that are based on a same immutable medical algorithm container image, e.g. where a same medical algorithm 33 is to be used in parallel.

According to some embodiments, the isolated runtime environment comprises a virtual machine, which can e.g. be based on an immutable installer (e.g. an ISO file).

According to some embodiments, the isolated runtime environment comprises physically isolated machine.

According to some embodiments, each isolated runtime environment provides its own processing capabilities, volatile memory, non-volatile memory, and networking resources. Each isolated runtime environment can e.g. be realized by using one or more separate kernel namespaces, separate virtual machines, and/or separate physical machines. According to some embodiments, the runtime environments of the medical algorithm modules 3 are isolated in the sense that none of the medical algorithm modules 3 can directly access the processing capabilities, volatile memory, non-volatile memory, and networking resources of any of the other medical algorithm modules 3, which can allow preventing the medical algorithm modules 3 from influencing each other and thus increasing the probability that the medical algorithm 33 works as intended. According to an example, the isolation can allow preventing a first medical algorithm module 3 from erroneously interacting with the memory used by a second medical algorithm module 3 and thereby can allow preventing an incorrect result by the medical algorithm 33 of the second medical algorithm module 3, in particular where the first medical algorithm module 3 and the second medical algorithm module 3 are based on a same immutable medical algorithm container image and/or use global variables.

Each medical algorithm module 3 comprises a medical algorithm application programing interface 30, the medical algorithm application programing interface 30 being designed for allowing to receive medically relevant data MRD from outside the medical algorithm module 3 and provide the medically relevant data MRD to the medical algorithm 33 of the medical algorithm module 3 and to provide, and in this sense output, results from the medical algorithm 33 to outside of the medical algorithm module 3. In particular, the medical algorithm application programing interface 30 can be designed for receiving results from the medical algorithm 33 and providing the received results to outside of the medical algorithm module 3.

According to some embodiments, the medical algorithm application programing interface 30 is designed for receiving the input for the medical algorithm 33, providing the input to the medical algorithm 33, receiving the output, e.g. a result, of the medical algorithm 33, and providing the output of the medical algorithm 33 to outside the medical algorithm module 3.

The proposed healthcare system 1 comprises a service module 2. The healthcare system 1 may be designed for using functionalities of the service module 2 for multiple, e.g. all, medical algorithm modules 3 of the healthcare system 1.

The service module 2 comprises a service application programing interface 20 being designed for interacting with the medical algorithm application programing interfaces 30 for allowing to provide medically relevant data MRD to the medical algorithm modules 3, e.g. from the service application programing interface 20 to the respective medical algorithm application programing interface 30; and to receive results of medical algorithms from the medical algorithm modules 3, e.g. from the respective medical algorithm application programing interface 30 to the service application programing interface 20.

The service application programing interface 20 is further designed for interacting with integration module(s) 4 for allowing to receive medically relevant data MRD from integration module(s) 4, to provide results of medical algorithms to integration module(s) 4, and to receive service data SD from integration module(s) 4.

According to some embodiments, the integration module 4 comprises a user portal (e.g. a webpage, an app) that allows a user to interact with the healthcare system 1, e.g. that allows a user to send medically relevant data MRD and/or service data SD to the healthcare system 1, and/or that allows a user to receive result(s) of medical algorithms from the healthcare system 1.

According to some embodiments, the integration module 4 comprises, is comprised in, and/or is connected to a laboratory information system (LIS), a hospital information system (HIS), a laboratory middleware, a hospital middleware, and/or an electronic medical record (EMR).

According to some embodiments, the integration module 4 is not comprised in the healthcare system 1.

The service application programing interface 20 can allow for exchanging data with the integration modules 4 as well as with the medical algorithm modules 3; this can e.g. allow a user of an integration module 4 to order and/or receive a result of a medical algorithm 33 available in the healthcare system 1.

According to some embodiments, the service data SD comprises not medically relevant data, in particular not medical data. According to some specific embodiments, the service data SD comprises no medically relevant data, in particular no medical data. The service data SD can e.g. comprise order data (e.g. an indication that a result from a medical algorithm 33 is ordered), authentication data (e.g. a user ID and/or a password and/or related information), data concerning to labelling information of a medical algorithm 33 of the healthcare system 1 (e.g. an indication that information on the intended use for a certain medical algorithm 33 in the healthcare system 1 is requested).

According to some embodiments, the service application programing interface 20 is further designed for interacting with one or more integration module(s) 4 for allowing to provide service data SD to the integration module(s) 4; this can e.g. allow for providing labelling information to the integration module(s) 4.

According to some embodiments, wherein the healthcare system 1 is designed such that the isolated runtime environment of a medical algorithm module 3 cannot directly access the computing and/or network resources of an isolated runtime environment of any other medical algorithm module 3.

According to some embodiments, the service module 2 resp. some or each of its components (e.g. the service sub-modules) is hosted in, e.g. comprised in, an isolated runtime environment. According to some specific embodiments, the isolated runtime environment is based on an immutable medical algorithm container image. This can allow increasing the possibility that the service module 2 and thereby the healthcare system 1 and thereby in particular the medical algorithms 33 work as intended.

According to some specific embodiments, the healthcare system 1 is designed such that the isolated runtime environment of a medical algorithm module 3 cannot directly access the computing and/or network resources of an isolated runtime environment of the service module 2 or any component thereof.

According to some specific embodiments, the healthcare system 1 is designed such that the isolated runtime environment of the service module 2 or any component thereof cannot directly access the computing and/or network resources of the isolated runtime environment of a medical algorithm module 3.

According to some embodiments, the healthcare system 1 is designed such that the medical algorithm modules 3 can communicate with each other via the service module 2, e.g. by transferring data from the medical algorithm application programing interface 30 of a first medical algorithm module 3 to the service application programing interface 20 and service application programing interface 20—the data possibly being transformed, e.g. reformatted—to the medical algorithm application programing interface 30 of a second medical algorithm module 3. This can e.g. allow a second medical algorithm 33 to use the output of a first medical algorithm 33 as an input.

According to some embodiments, the service module 2 is designed for processing the medically relevant data MRD and the results of the medical algorithms without adding medical value to the medically relevant data MRD or the results. The service module 2 may be designed for processing the medically relevant data MRD without adding medical value (e.g. encrypting/decrypting the medically relevant data MRD, reformatting the medically relevant data MRD, and/or adapting the medically relevant data MRD so that it can be used with one or more of the medical algorithms 33 available in the healthcare system 1).

The proposed healthcare system 1 can allow for separating the functionalities in the context of providing the result(s) between the service module 2 and the medical algorithm modules 3. The service module 2 can e.g. provide for service functionalities that can potentially be used in the context of multiple or even all medical algorithm modules 3, such as service functionalities concerning encryption, (cyber) security, authorization, and/or activity tracking. The service module 2 can comprise one or more service sub-modules 21, 22, 23, 24, 25 for providing service functionality. According to some embodiments, the healthcare system 1 is designed so that the service module 2 and/or its service sub-modules 21, 22, 23, 24, 25 can be started/terminated/updated independently of the medical algorithm module 3. According to some embodiments, the healthcare system 1 is designed so that the medical algorithm modules 3 can be started/terminated/updated independently of each other.

According to some embodiments, the service module 2 comprises a service sub-module in form of an encryption module 21 designed for decrypting and/or encrypting data, e.g. for exchanging data with an integration module 4. According to some specific embodiments, the encryption module 21 is designed for encrypting and/or decrypting medically relevant data MRD, results of medical algorithms 33, and/or service data SD. According to some more specific embodiments, the encryption module 21 is designed for decrypting received medically relevant data MRD and encrypting results of medical algorithms 33. Encrypting/decrypting can be applied at various stages of data processing in the healthcare system 1, e.g. a decryption of data when the data is first received in the healthcare system 1, and/or an encryption of data before the data is to leave the healthcare system 1 and/or to be stored. Encryption may be used for the communication with modules external to the healthcare system 1 and/or in between modules within the healthcare system 1. Encrypting/decrypting can be performed using certificates. According to some specific embodiments, none of the medical algorithm modules 3 comprises an encryption/decryption functionality. An encryption/decryption functionality dedicated to a specific medical algorithm module 3 may be provided (in the healthcare system 1) by using a dedicated module, e.g. a so-called sidecar.

According to some embodiments, the service module 2 comprises a service sub-module in form of a security module 22 designed for monitoring possible security risks for the healthcare system 1 and in particular for the medical algorithms 33. The security module 22 may e.g. be designed for issuing an alert when a possible security risk has been detected. According to some specific embodiments, the security module 22 is designed for controlling the network traffic of the healthcare system 1, in particular the incoming network traffic. The security module 22 may be designed for providing a firewall functionality. The security module 22 may e.g. be designed for enforcing a pre-defined set of rules for the network traffic (e.g. for attempting to prevent Denial-of-service attacks). The monitoring/controlling may be performed using received service data SD, e.g. information on the network traffic of an integration module 4. According to some specific embodiments, none of the medical algorithm modules 3 comprises a security functionality.

According to some embodiments, the service module 2 comprises a service sub-module in form of an authorization module 23 designed for authorizing, using received service data SD, the use of at least one of the medical algorithms 33. The authorization module 23 may comprise and/or may be connected to an integration module 4 comprising an authorization server; the authorization server may be designed for providing a SSO functionality or an OpenID functionality. According to some specific embodiments, the authorization module 23 may comprise an authentication module designed for authenticating, using received service data SD, a user (resp. an organization of a user). The service data SD used by the authorization module 23 (e.g. by an authentication module thereof) may e.g. comprise a user ID, a password, a token (e.g. an access token), and/or an indication that a user is authorized to use a specific medical algorithm 33 (where such indication is e.g. provided by an authentication server). The authorization module 23 can be designed to authorize the use of an medical algorithm 33 based on an authentication of a user requesting said use. According to some specific embodiments, none of the medical algorithm modules 3 comprises an authorization functionality.

According to some embodiments, the service module 2 comprises a service sub-module in form of an activity tracking module 24 designed for recording at least some activities in the context of the medical algorithms 33, e.g. that a medical algorithm 33 was executed and/or that a medical algorithm 33 was available. The recorded data may e.g. comprise data based on medically relevant data MRD and the version of the medical algorithm 33 executed using this medically relevant data MRD; this can e.g. allow re-executing the medical algorithm 33 or executing an updated version of the medical algorithm 33, e.g. when a possible error with the original result has been detected. The recorded data may comprise log files, in particular log files concerning problems that have occurred within the healthcare system 1, in particular problems that have occurred in connection with the medical algorithm modules 3/medical algorithms 33. The recorded data can e.g. allow for improving and/or documenting the quality of the results of the medical algorithms 33. The recorded data may e.g. comprise data concerning the resources used by the healthcare system 1, in particular the resources used by the medical algorithm modules 3 of healthcare system 1. The recorded data can e.g. allow for improving the inner functioning of the healthcare system 1. The recorded data may be stored within the healthcare system 1 and/or outside the healthcare system 1 (e.g. at a dedicated external server). According to some specific embodiments, none of the medical algorithm modules 3 comprises an activity tracking functionality.

According to some embodiments, none of the medical algorithm modules 3 comprises a security functionality, an authorization functionality, or an activity tracking functionality; instead such functionalities may be provided by the service module 2.

The medical algorithm 33 may e.g. be designed for enriching quantitative medical data created based on at least one diagnostic measurement method (e.g. in-vitro diagnostic laboratory measurement results). The medical algorithm 33 may e.g. comprise a risk-score calculated using a (possibly well-known) mathematical formula.

The medical algorithms 33 may e.g. comprise a trained artificial intelligence.

In case where the medical algorithm module 3 is based on an immutable medical algorithm container image, the medical algorithm 33 cannot be altered and thus the medical algorithm 33 may not comprise an artificial intelligence that is designed for autonomous learning. However, a medical algorithm container image comprising a trained artificial intelligence may be replaced by a medical algorithm container image comprising an improved (e.g. further and/or differently trained) version of that trained artificial intelligence, and newly created medical algorithm modules 3 may be based on the replacing medical algorithm container image. Furthermore, the healthcare system 1 may comprise additional modules other than the two or more medical algorithm modules 3, and these additional modules (e.g. additional medical modules) may comprise an artificial intelligence that is designed for autonomous learning. An artificial intelligence designed for autonomous learning may e.g. be used in a usage prediction module 25j of the service module 2.

The medical algorithms' results may be deemed medical insights and can e.g. be used for the purpose of prevention, diagnosis, treatment, and/or monitoring of a medical problem of a patient. Depending on the respective details, a medical algorithm 33 may add medical value to the medically relevant data MRD so that it is classified, by the relevant authorities, as a medical device of a certain kind. The healthcare system 1 can e.g. allow supporting physicians to use medical algorithms in their daily work to support their medical decision making (e.g. planning a treatment, a surgery, follow up tests)

According to some embodiments, the medical algorithms 33 of the two or more medical algorithm modules 3 of the healthcare system 1 are of non-image-processing type, i.e. are not designed for creating a result by using images (e.g. X-ray images or MRI images) to create a result.

According to some embodiments, each of the medical algorithms 33 of the two or more medical algorithm modules 3 of the healthcare system 1 is designed for processing medically relevant data MRD comprising quantitative medical data, i.e. is designed for creating a result by using at least quantitative medical data (possibly together with further medically relevant data MRD). However, the healthcare system 1 may comprise additional modules that comprise medical algorithms not designed for processing quantitative medical data, e.g. medical algorithms that are designed for processing qualitative medical data together with data concerning a patient without processing quantitative medical data.

FIG. 1 illustrates a possible implementation of the proposed healthcare system 1 for providing medical insights by receiving medically relevant data (MRD) and providing results of medical algorithms using the medically relevant data MRD, the medically relevant data MRD comprising quantitative medical data created based on at least one diagnostic measurement method, wherein the healthcare system 1 comprises two or more medical algorithm modules 3 and a service module 2;

wherein the medical algorithm modules 3 each comprises a medical algorithm 33, the medical algorithm 33 being designed for algorithmically creating results using medically relevant data MRD, each is hosted in, e.g. comprised in, an isolated runtime environment for its medical algorithm 33 (which e.g. can be based on an immutable medical algorithm container image), each comprises a medical algorithm application programing interface 30, the medical algorithm application programing interface 30 being designed for allowing to receive medically relevant data MRD from outside the medical algorithm module 3 and provide the medically relevant data MRD to the medical algorithm 33 of the medical algorithm module 3, and to provide results from the medical algorithm 33 to outside of the medical algorithm module 3;

wherein the service module 2 comprises a service application programing interface 20, the service application programing interface 20 being designed for interacting with the medical algorithm application programing interfaces 30 for allowing to provide medically relevant data MRD to the medical algorithm module 3, and to receive results of medical algorithms from the medical algorithm module 3, the service application programing interface 20 being designed for interacting with integration module(s) 4 for allowing to receive medically relevant data MRD from integration module(s) 4, to provide results of medical algorithms to integration module(s) 4, and to receive service data SD from integration module (s) 4; and wherein the service module 2 comprises an encryption module 21 designed for decrypting and/or encrypting data, a security module 22 designed for monitoring possible security risks for the medical algorithms 33, an authorization module 23 designed for authorizing, using received service data SD, the use of at least one of the medical algorithms 33, and an activity tracking module 24 designed for recording at least some activities in the context of the medical algorithms 33.

A medical algorithm can be understood as an algorithm producing a result that can be used in the field of medical diagnostics, in particular for the purpose of prevention, diagnosis, treatment, and/or monitoring of a medical problem of a patient. A medical algorithm can for example be understood as a computation method, formula, statistical survey, nomogram, or look-up table, useful in healthcare. In particular, a medical algorithm may be an artificial machine learning algorithm being trained using training data comprising medically relevant data. Medical algorithms can e.g. be understood as set out at: en.wikipedia.org/wiki/Medical_algorithm.

A medical insight can be understood as information which can be used by a physician for medical purposes, in particular for the purpose of prevention, diagnosis, treatment, and/or monitoring of a medical problem of a patient. A medical insight can e.g. be a result of a medical algorithm, possibly in combination with medically relevant data used for gaining this result, and/or a finding based on a result of a medical algorithm (possibly in combination with medically relevant data used for gaining this result).

As illustrated in FIG. 1, a user may have medically relevant data MRD comprising quantitative medical data created based on at least one diagnostic measurement method measured, e.g. using one or more in-vitro diagnostic analytical instruments 9. The user may transmit the medically relevant data MRD and service data SD (e.g. authentication data and an indication which medical algorithm's result is ordered) via the integration module 4, e.g. a browser-based portal, to the healthcare system 1 and thereby orders a result of the indicated medical algorithm 33 based on the transmitted medically relevant data MRD. The user may interact with the integration module 4 using an integration graphical user interface 48 of the integration module 4 and the integration module 4 may transmit the medically relevant data MRD and the service data SD via an integration application programing interface 40 of the integration module 4 to the service application programing interface 20 of the service module 2. The service module 2 may execute certain service functionalities in connection with the execution of that request, e.g. service functionalities concerning decryption/encryption, security, authorization, and activity tracking. The service module 2, again via its service application programing interface 20, may forward the, possibly adapted (e.g. decrypted and/or reformatted), medically relevant data MRD to the medical algorithm application programing interface 30 of one of the medical algorithm modules 3 that comprises the ordered medical algorithm 33, from where the medically relevant data MRD may be provided to the medical algorithm 33. After calculating the result using the provided medically relevant data MRD, the result may be provided from the medical algorithm 33 to the medical algorithm application programing interface 30, from the medical algorithm application programing interface 30 to the service application programing interface 20, from service application programing interface 20 to the integration application programing interface 40, from integration application programing interface 40 to integration graphical user interface 48 where it may be displayed (and thereby outputted) to the user.

The healthcare system 1 is designed so that the external communication can be performed via the service module 2, which can e.g. allow for designing the healthcare system 1 such that the medical algorithm modules 3 are not directly exposed to the integration module 4 or any other system outside the healthcare system 1, which in turn may e.g. support the protection of the integrity of the medical algorithms 33.

The healthcare system 1 is designed so that some services that are used for processing the orders for the medical algorithms 33 may not be part of the individual medical algorithm module 3 but may be part of the shared service module 2 instead. This can e.g. allow for reducing the exposure to potential vulnerabilities, for improving the stability of the healthcare system 1, and/or for improving the efficiency of the resource usage within the healthcare system 1. Developers of medical algorithm 33 may not have to deal with the service functionalities, but e.g. rely on defined interfaces. The medical algorithm modules 3 and the service module 2 (resp. its sub-modules) may be updated independently from each other, which can e.g. allow for reducing downtime and/or reducing errors.

According to some embodiments, the healthcare system 1 is designed such that some, e.g. each, of the medical algorithm modules 3 are not directly accessible from the internet (e.g. where no public IP addresses are allocated to the medical algorithm modules 3).

Figure 2:
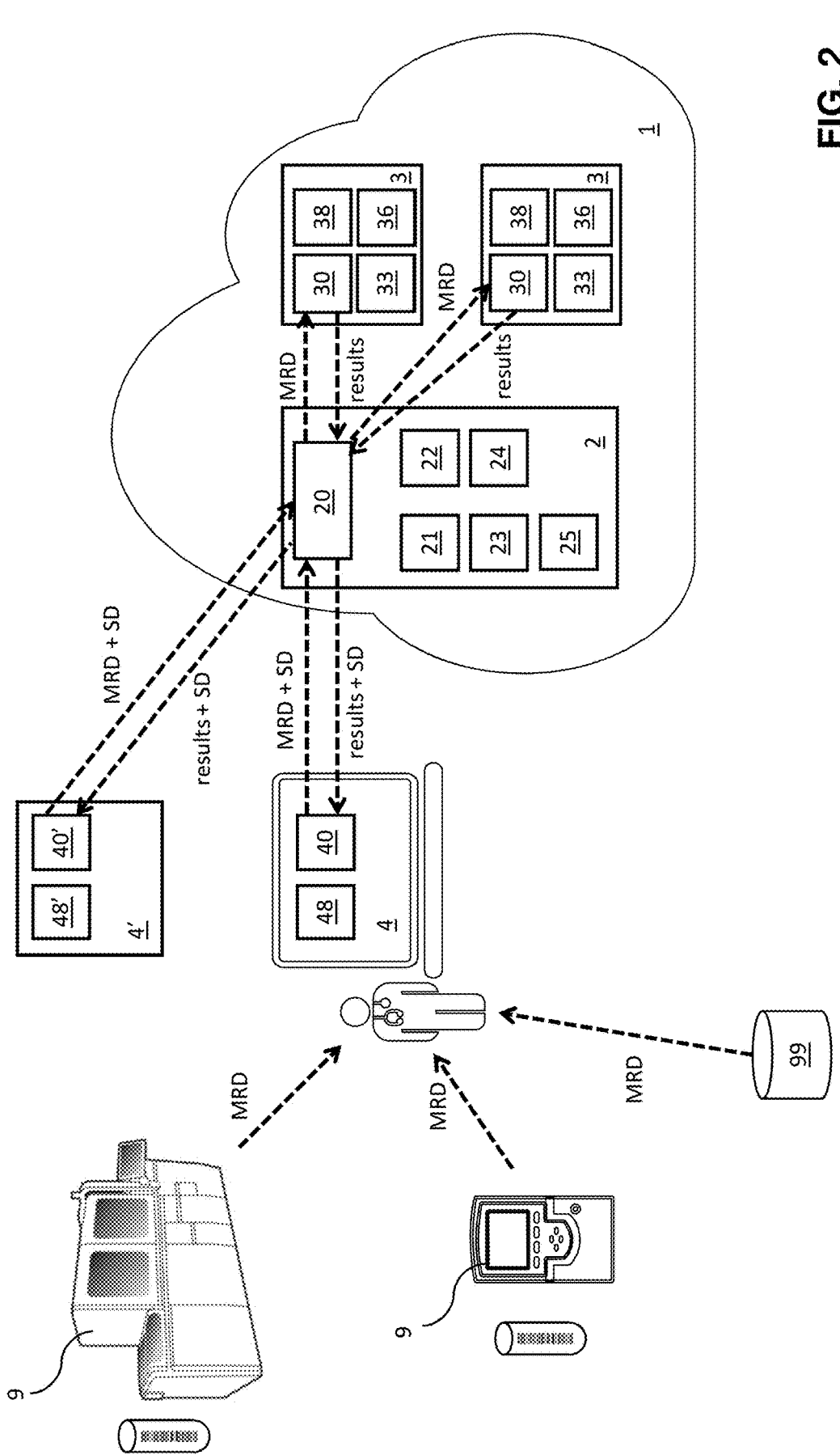
FIG. 2 shows a healthcare system and additional systems connected thereto.

FIG. 2 illustrates a further possible implementation of the proposed healthcare system 1. As indicated in FIG. 2, the medically relevant data MRD may comprise data originating from a data source other than an in-vitro diagnostic analytical instruments 9, said other data source e.g. being a database 99. The database may e.g. comprise medical data (e.g. quantitative in-vivo medical data and/or qualitative medical data) and/or data concerning a patient.

As further indicated in FIG. 2, two or more integration module 4 may be connected to, e.g. designed for exchanging data with, the healthcare system 1. A first integration module 4 may e.g. be used by a user to order the result of a certain medical algorithm 33 where at least part of the medically relevant data MRD and/or the service data SD is provided by a second integration module 4' and/or a result is to be provided to the second integration module 4'. According to an example, a user uses a first integration module 4 for ordering a result for which all the medically relevant data MRD is provided by a second integration module 4'; service data SD comprising an indication of the order and the user's identity is transferred from the first integration module 4 to the service module 2; medically relevant data MRD and service data SD comprising an indication that the medically relevant data MRD is transferred from a reliable source (e.g. using a certificate) is transferred from the second integration module 4' to the service module 2; the service module 2 processes the service data SD and transfers the medically relevant data MRD (that e.g. has been decrypted and reformatted by the service module 2) to a medical algorithm module 3 and in return receives a result from the medical algorithm 33 of the medical algorithm module 3, which the service module 2 then transmits the result (that e.g. has been reformatted and encrypted by the service module 2) to the first integration module 4, where the result can be outputted to the user.

According to some embodiments, some, e.g. each, of the medical algorithm modules 3 are designed to be usable independent of the service module 2. This can e.g. allow for using the medical algorithm module 3 in two different ways: firstly by using the service module 2 and secondly without using the service module 2. In particular, some, e.g. each, of the medical algorithm modules 3 may be designed for receiving the medically relevant data MRD and providing the results of its medical algorithm 33.

According to some embodiments, some, e.g. each, of the medical algorithm modules 3 comprises a medical algorithm graphical user interface 38, the medical algorithm graphical user interface 38 being designed for allowing
    to input, e.g. by a user, medically relevant data MRD to the medical algorithm module 3 and to provide the medically relevant data MRD to the medical algorithm 33 of the medical algorithm module 3, and
    to display, e.g. to a user, results from the medical algorithm 33.

According to some embodiments, some, e.g. each, of the medical algorithm module 3 comprises an input validation module 36 designed for validating the medically relevant data MRD provided to the medical algorithm module 3; the input validation module 36 can further be designed for providing medically relevant data MRD to the medical algorithm 33 only in case the medically relevant data MRD is validated. The validation can e.g. be based on the provided medically relevant data MRD meet a defined input criteria (e.g. allowed ranges for quantitative data, an allowed format, etc.).

Figure 3:
FIG. 3 shows a direct interaction between an integration module and a medical algorithm module.

FIG. 3 illustrates an example how an integration module 4 may directly interact with a medical algorithm module 3 independently of the service module 2. In this example, an integration application programing interface 40 of the integration module 4 directly interacts with the medical algorithm graphical user interface 38 of the medical algorithm module 3, e.g. for inputting medically relevant data MRD. An input validation module 36 may be used to validate the inputted medically relevant data MRD before the medical algorithm 33 processes the medically relevant data MRD. Using a medical algorithm application programing interface 30 for inputting data instead of a medical algorithm graphical user interface 38 can e.g. allow for reducing the risk of errors related to manual input. However, providing a medical algorithm graphical user interface 38 in addition to the medical algorithm application programing interface 30 can be beneficial, e.g. for having a secondary/back-up input option.

FIG. 4 illustrates several examples of how an integration module 4 may directly interact with a medical algorithm module 3 without using the service module 2. The example of FIG. 4a corresponds to that of FIG. 3, where an integration application programing interface 40 of an integration module 4 communicates with a medical algorithm application programing interface 30 of a medical algorithm module 3. In the example of FIG. 4b, an integration graphical user interface 48 of an integration module 4 communicates with a medical algorithm graphical user interface 38 of a medical algorithm module 3. In the example of FIG. 4c, an integration graphical user interface 48 of an integration module 4 communicates with a medical algorithm application programing interface 30 of a medical algorithm module 3. In the example of FIG. 4d, an integration application programing interface 40 of an integration module 4 communicates with a medical algorithm graphical user interface 38 of a medical algorithm module 3. The communication model may depend on the details of the integration of the integration module 4 and possibly be different for different tasks.

According to some embodiments, the healthcare system 1 comprises at least one medical algorithm adapter 6 designed for connecting with an external medical algorithm 73 comprised in an external application 7, the medical algorithm adapter 6 comprising an adapter application programing interface 60 designed for allowing
    to receive medically relevant data MRD from the service module 2, e.g. via the service application programing interface 20,
    to provide (the received) medically relevant data MRD to the external application 7, e.g. via an external application programing interface 70 of the external application 7,
    to receive results of the external medical algorithm 73 from the external application 7, and
    to provide (the received) results of the external medical algorithm 73 to the service module 2, e.g. via the service application programing interface 20.

According to some specific embodiments, the at least one medical algorithm adapter 6 is hosted in, e.g. comprised in, an isolated runtime environment (that can e.g. be based on an immutable medical algorithm adapter container image).

Figure 5:
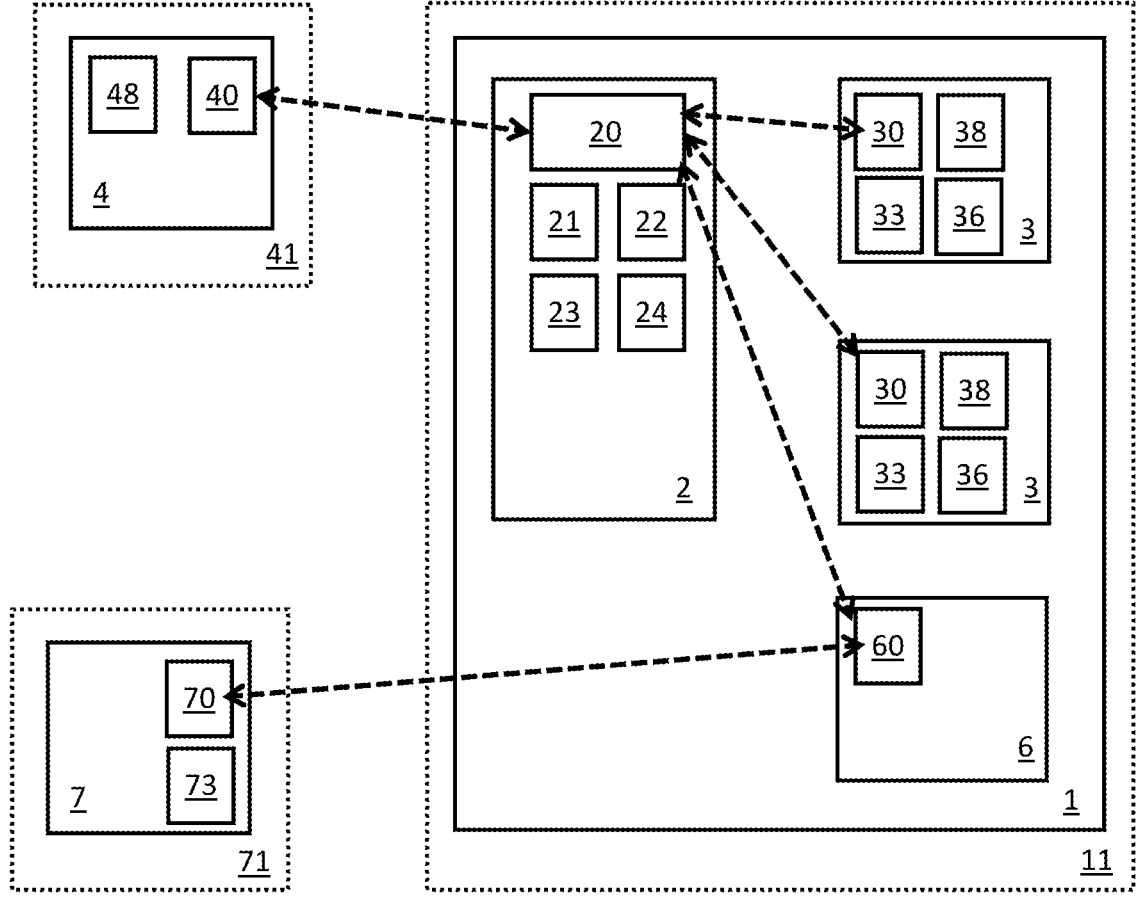
FIG. 5 shows a healthcare system using a medical algorithm adapter 6 to connect to an external medical algorithm.

FIG. 5 illustrates an example of a healthcare system 1 comprising a medical algorithm adapter 6. As illustrated, such external medical algorithm 73 may be ordered via an integration module 4; the medically relevant data MRD and service data SD may be transferred from the integration module 4 to the service module 2, the service module 2 may be process the service data SD and transmit the medically relevant data MRD to the medical algorithm adapter 6; the medical algorithm adapter 6 may transfer the medically relevant data MRD to an external application 7 comprising the ordered external medical algorithm 73; the external medical algorithm 73 may create a result using the medically relevant data MRD; the external application 7 may transfer the result to the medical algorithm adapter 6; the medical algorithm adapter 6 may transfer the result to the service module 2; and the service module 2 may transfer to the integration module 4.

From the perspective of the integration module 4 and the service module 2, the process for executing the external medical algorithm 73 may look just like as if dealing with an internal medical algorithm 33. The medical algorithm adapter 6 may allow for using, with the healthcare system 1, medical algorithms that were not designed to be compatible with the healthcare system 1. Since, from the perspective of the other components, the medical algorithm adapter 6 resp. external medical algorithm 73 can play a same or at least a similar role as the medical algorithm module 3 resp. medical algorithm 33, embodiments and features addressing the medical algorithm module 3 resp. medical algorithm 33 may—if compatible and, if compatible, to the degree compatible and/or with necessary/advantageous adaptations— also be realized/used in connection with the medical algorithm adapter 6 resp. external medical algorithm 73.

As indicated in FIG. 5, the healthcare system 1 and the external application 7 may be in different protected networks, e.g. the healthcare system 1 in a first protected network 11 and the external application 7 in a third protected network 71. In the illustrated example of FIG. 5, the integration module 4 is comprised in yet another protected network, e.g. in a second protected network 41.

A protected network may be a (computer) network that has a barrier between it and outside network(s), e.g. the internet. The protected network may be considered a trusted, secure internal network and the other outside network(s) may be assumed not to be secure or trusted. A protected network may e.g. be protected by a firewall or another network protection means.

Figure 6:
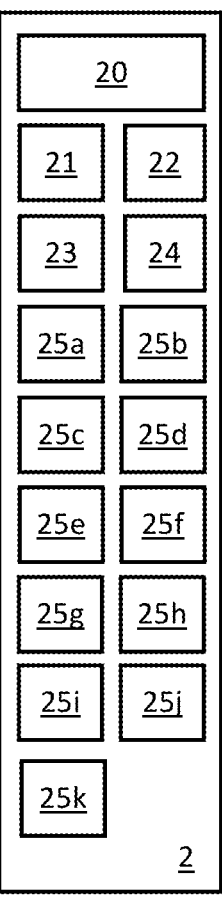
FIG. 6 shows additional service sub-modules.

FIG. 6 illustrates a plurality of possible additional service sub-modules 25 of the service module 2. The service sub-modules may e.g. provide various functionalities that are not specific to the individual medical algorithm modules 3, but e.g. concern a plurality of medical algorithm modules 3, such as aspects related to management, infrastructure, or functional services.

According to some embodiments, the service module 2 comprises a medical algorithm catalogue database 25a designed for providing information related to the medical algorithms available via the healthcare system 1, e.g. the medical algorithms 33 and the external medical algorithms 73. The medical algorithm catalogue database 25a may e.g. be designed for providing an overview over the available medical algorithms, possibly including information on the respective medical algorithm;

for providing and/or linking to supplementary information related to the medical algorithms (e.g. articles, papers, studies/study data, etc.);

as a marketplace for the medical algorithms (e.g. allow for initiating deployment of medical algorithm container images and/or access to medical algorithms; provide information on billing/subscription models); and/or for only providing information related to the medical algorithms available for the respective user (e.g. only related to those medical algorithms that have been approved by the relevant authorities for the territory the user is located in).

According to some embodiments, the service module 2 comprises a medical algorithm search module 25b designed for searching the medical algorithms available via the healthcare system 1. The medical algorithm search module 25b may e.g. be further designed for grouping the medical algorithms into groups (e.g. for different disease types/areas). may e.g. be further designed for filtering the medical algorithms (e.g. according to different disease types/areas). The medical algorithm search module 25b can e.g. be comprised in the medical algorithm catalogue database 25a and provide a search functionality for the medical algorithm catalogue database 25a.

According to some embodiments, the service module 2 comprises a product labelling information module 25c designed for providing product labelling information on and/or by the respective manufacturer of the medical algorithms available via the healthcare system 1. The product labelling information may e.g. comprise information on the intended use, market approval information (such as the CE mark), a global registration number for medical devices, version, etc. The product labelling information module 25c can e.g. be comprised in the medical algorithm catalogue database 25a.

According to some embodiments, the service module 2 comprises a user management module 25d designed for managing user access to the medical algorithms available via the healthcare system 1.

According to some embodiments, the service module 2 comprises a billing module 25e designed for managing billing information on the use of at least one of the medical algorithms available via the healthcare system 1. The billing module 25e can e.g. be comprised in the user management module 25d.

According to some embodiments, the service module 2 comprises a subscription module 25f designed for managing subscriptions for using at least one of the medical algorithms available via the healthcare system 1. The subscription module 25f can e.g. be comprised in the user management module 25d.

According to some embodiments, the service module 2 comprises a usage statistics module 25g designed providing usage statistics, e.g. based on tracked usage activities. The usage statistics module 25g can e.g. be comprised in the user management module 25d.

According to some embodiments, the service module 2 comprises a resource management module 25h designed for allocating computing and/or networking resources to the components of the healthcare system 1, in particular to the medical algorithm module 3. The resource management module 25h may be designed for instance management, e.g. for (re-)starting instances, health checks, processor allocation, memory allocation, server allocation, network services (such as IP address routing, server resolution, and/or DNS services, etc.).

According to some embodiments, the service module 2 comprises a resource monitoring module 25i designed for monitoring computing and/or networking resources within the healthcare system 1. The resource monitoring module 25i may e.g. be designed for monitoring run time statistics, such as processor usage and/or memory usage. The resource monitoring module 25i can e.g. be comprised in the resource management module 25h.

According to some embodiments, the service module 2 comprises a usage prediction module 25j designed for predicting the upcoming usage of components, e.g. container instances, of the healthcare system 1, in particular the medical algorithm modules 3, and for starting and/or ending components, e.g. container instances, of the healthcare system 1, in particular the medical algorithm modules 3, according to the prediction of the upcoming usage. The usage prediction module 25j may e.g. use an artificial intelligence; the artificial intelligence may e.g. be trained using historic data; the artificial intelligence may e.g. be designed for autonomously learning (e.g. based on the actual usage within the healthcare system 1). The usage prediction module 25j can e.g. allow for improving the response time and/or stability of the healthcare system 1. The usage prediction module 25j can e.g. be comprised in the resource management module 25h.

According to some embodiments, the service module 2 comprises an input validation service module 25k designed for a validation of the medically relevant data MRD provided to the healthcare system 1 on a service level. This validation may e.g. comprise dummy-check(s), minimum check(s) that check if the medically relevant data MRD meets minimum requirements (e.g. requirements common to all medical algorithms available in the healthcare system 1), and/or algorithm specific check(s) (e.g. some or all validation criteria of a specific medical algorithm; the criteria may be provided to the input validation service module 25k via meta module(s) of the medical algorithm(s)). The service module 2 may be designed to provide medically relevant data MRD to the medical algorithm modules 3 only if this validation of the respective medically relevant data MRD has been successful.

A further sub-module 25 can e.g. be a data transformation module for transforming data, e.g. for transforming medically relevant data prior to providing the medically relevant data to a medical algorithm module and/or for transforming a result of a medical algorithm prior to providing the result to an integration module. The data transformation module can be designed for transforming data by (re-)formatting data, e.g. by translating the data from a first data format to a second data format (e.g. a file with CSV values can be transformed into an XML file), in particular to a second data format that is required by some specific medical algorithm module or some specific integration module. The data transformation module can be designed for transforming data by altering the precision of numerical values, e.g. rounding to a different decimal digit or transforming a date of birth which is represented by a values representing a day, a month, and a year to a value that just represents a year. The data transformation module can be designed for transforming data from numerical data (e.g. date of birth) into category data (e.g. adult, teenager, infant). The data transformation module can use transformation rules for transforming the data so that it can be suitable input data for the intended recipient, e.g. a medical algorithm and/or an integration module. The service module can comprise a storage system for storing the rules. Each stored rule can be assigned to a selection of recipients, e.g. one or more medical algorithm modules and/or one or more integration modules. A rule generation module being part of the service module (e.g. being part of the data transformation module) and/or being part of an integration module can support a user in creating rules for particular medical algorithms. The rules generation module can comprise a machine learning algorithm that has been trained using suitable input and output data, e.g. data that is required/provided by some specific integration module and/or data that is required/provided by some specific medial algorithm module.

A further sub-module 25 can e.g. be a signing module for (digitally) signing at least some of the results of the medical algorithms. The signing module can be designed for (digitally) signing at least one result of at least one medical algorithm, thereby allowing to verify that the result(s) has not been tampered with. The signing module can be designed for creating a signed data package, the signed data package comprising the result and a signature component. The signature component can e.g. be an encrypted file, wherein the file is encrypted using a (private) key of an asymmetric key pair; the encrypted file can later be decrypted using a (public) key of the asymmetric key pair. The file can e.g. comprise the result or data being created using the result, e.g. the output value of the result being inputted to a one-way function (such as e.g. a hash function).

A further sub-module 25 can e.g. be a data associating module for associating data, e.g. for associating data relating to a same patient. This can allowing identifying multiple sets of medically relevant data and/or medical results that relate to a same patient. According to some examples, the data associating modules stores data and respective patient IDs and associates data relating to the same patient ID; according to some specific embodiments, the patient ID by itself does not allow for identifying a patient. Associating data that relate to a same patient can allow creating a data set in which multiple data entries for a same person are associated with each other; such a data set can e.g. be used for research (e.g. for discovering new medical knowledge and/or training medical machine learning algorithms) and/or as input for medical algorithm modules.

The healthcare system 1 can be designed for allowing users to input further information, e.g. a feedback, a diagnosis, and/or information on a long-term development of a patient, and the data associating module can be designed for associating that further information with other data, e.g. medically relevant data and/or medical results associated with a same patient. The further information can e.g. be inputted using an integration module 4.

Figure 7:
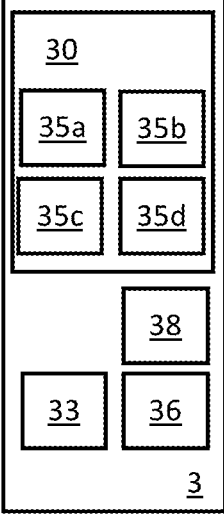
FIG. 7 shows various interface module.

FIG. 7 illustrates a plurality of possible interface modules 35 of the medical algorithm module 3.

According to some embodiments, some, e.g. each, of the medical algorithm modules 3, in particular the respective medical algorithm application programing interface 30 and/or medical algorithm graphical user interface 38, comprise, a labelling information module 35a designed for providing labelling information. The labelling information can comprise information required by regulation to be provided with a medical device of a certain type. The labelling information can e.g. comprise a graphical representation of information on a name of the medical algorithm, a legal manufacturer, an intended use, a serial number, and/or a version number. The labelling information can comprise one or more icons (such as e.g. the CE mark, or the IVD symbol).

According to some embodiments, some, e.g. each, of the medical algorithm modules 3, in particular the respective medical algorithm application programing interface 30 and/or medical algorithm graphical user interface 38, comprise a meta module 35b designed for providing information on a structured definition of the medical algorithm 33 and its input and output; the information can e.g. comprise a format and/or a unit in which the input has to be inputter and/or in which the output is inputted, and/or validation criteria.

According to some embodiments, some, e.g. each, of the medical algorithm modules 3, in particular the respective medical algorithm application programing interface 30 and/or medical algorithm graphical user interface 38, comprise a ready module 35c designed for providing information to indicate that the medical algorithm 33 of the medical algorithm module 3 is ready to serve requests.

According to some embodiments, some, e.g. each, of the medical algorithm modules 3, in particular the respective medical algorithm application programing interface 30 and/or medical algorithm graphical user interface 38, comprise an alive module 35d designed for providing information to indicate that the medical algorithm 33 of the medical algorithm module 3 is running.

The modules of the healthcare system 1 (e.g. the medical algorithm modules 3, the service module 2, the medical algorithm adapter 6, or respective sub-modules thereof) may be container instances (also referred to as container modules) based on immutable container images, e.g. container images that are created in accordance with the Open Container Initiative Image Format Specification. The containers may e.g. be deployed in a cluster of (virtual) machines (e.g. a cloud system such as Amazon Web Service) that may be managed by a container orchestrator such as Kubernetes. Two modules may be based on a same immutable container image, e.g. two medical algorithm modules 3 or two sub-modules of service module 2, e.g. where multiple instances are deemed useful or effective. A container instance may comprise its own file system and if the images are immutable, any temporary data stored in said file system is lost when the container instance is terminated. Each container instance may use its own libraries separated from the libraries of other container instance.

Further proposed is a healthcare system combination 100 of the proposed healthcare system 1 and an integration module 4, wherein the integration module 4 comprises an integration module interface 40, 48 designed for providing medically relevant data MRD to the healthcare system 1 (e.g. via the service application programing interface 20), receiving results of medical algorithms from the healthcare system 1 (e.g. via the service application programing interface 20), providing service data SD to the healthcare system 1 (e.g. via the service application programing interface 20).

According to some embodiments, the integration module interface 40, 48 is further designed for receiving service data SD from the healthcare system 1 (e.g. via the service application programing interface 20); the service data SD can e.g. comprise an indication that an ordered result cannot be delivered because the provided medically relevant data MRD could not be validated for the ordered medical algorithm.

According to some embodiments, the integration module 4 comprises a portal, e.g. realized using an app or a webpage/browser.

According to some embodiments, the integration module 4 comprises, is comprised in, and/or is connected to a laboratory information system (LIS), a hospital information system (HIS), a laboratory middleware, a hospital middleware, and/or an electronic medical record (EMR). This can e.g. allow for an integration of the healthcare system 1 to the respective IT systems, e.g. for integrating automatic workflows. According to an example, a laboratory middleware is designed to, in certain cases (e.g. depending on the respective work order), automatically request a result of a medical algorithm and provide respective medically relevant data MRD comprising quantitative medical data in the form of laboratory results after the laboratory results have become available, and then use the result of the medical algorithm to enhance the laboratory results, and provide the enhanced laboratory result to an LIS and/or an EMR.

According to some embodiments, the integration module 4 comprises an adapting unit for adapting, e.g. reformatting, data to be transmitted to and/or received from the healthcare system 1. The adapting unit may support integration of the healthcare system 1 with another IT system.

According to some embodiments, the integration module interface 40, 48 comprises an integration application programing interface 40 designed for interacting with the service application programing interface 20 for allowing to provide medically relevant data MRD and service data SD from the integration module 4 to the service module 2, and to receive results of medical algorithms from the service module 2 to the integration module 4.

According to some embodiments, the integration module interface 40, 48 comprises an integration graphical user interface 48 designed for allowing a user to input and receive data, in particular for allowing a user to input an order for a result of a medical algorithm 33 of the healthcare system 1 (and—optionally—medically relevant data MRD and/or service data SD), and to display results from the medical algorithm 33 to a user.

According to some embodiments, the integration module 4 comprises an autofill module for automatically filling at least some fields for ordering the result of the medical algorithms. The integration module might be designed to monitor the integration graphical user interface and, based on observed input, to determine input to be filled automatically. According to an example, a user inputs a patient ID to a first field of the integration graphical user interface and the autofill module automatically fills other fields of the integration graphical user interface, e.g. with medically relevant data associated with that patient ID. According to some embodiments, the typography of the automatically filled in data is—at least initially—different from the typography of manually inputted data. According to some embodiments, the autofill module is connected to a data source, e.g. an electronic medical record (EMR), a laboratory information system (LIS), and/or a hospital information system (HIS); according to some specific embodiments, the automatically filled input is derived, e.g. read, from the EMR, the LIS, the HIS, and/or other sources. Automatically filling in data, especially medically relevant data, cannot only allow to use the system in a faster and more convenient manner, but also to reduce risk of false input.

Figure 8:
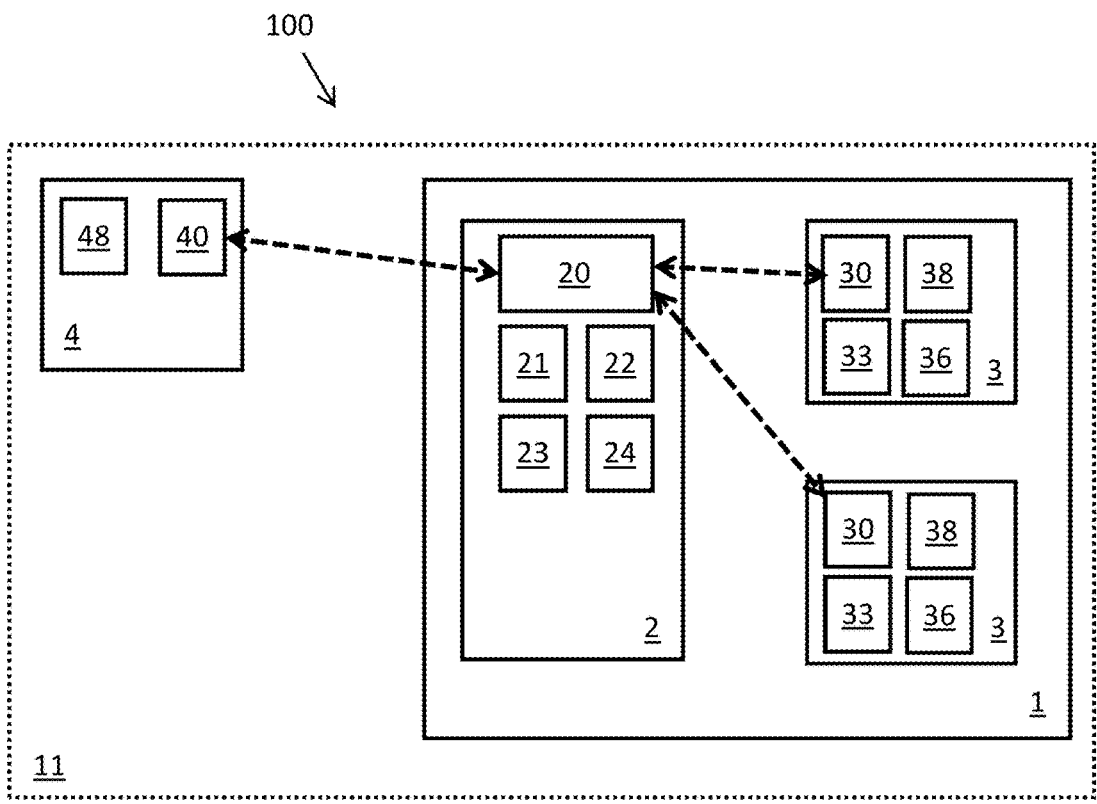
FIG. 8 shows a healthcare system combination deployed in a single protected network.

FIG. 8 illustrates a possible implementation of the proposed healthcare system combination 100. In the depicted example, the integration module 4 comprises both, an integration application programing interface 40 and an integration graphical user interface 48, e.g. where the integration application programing interface 40 is used for the communication with the healthcare system 1, e.g. the service application programing interface 20 thereof, and the integration graphical user interface 48 is used for communication with a user.

According to some embodiments, the integration graphical user interface 48 comprises a dashboard designed for displaying information related to the medical algorithms available via the healthcare system 1. The dashboard may e.g. be designed for displaying patient information (e.g. name) and medical algorithms' results for that patient.

Figure 9:
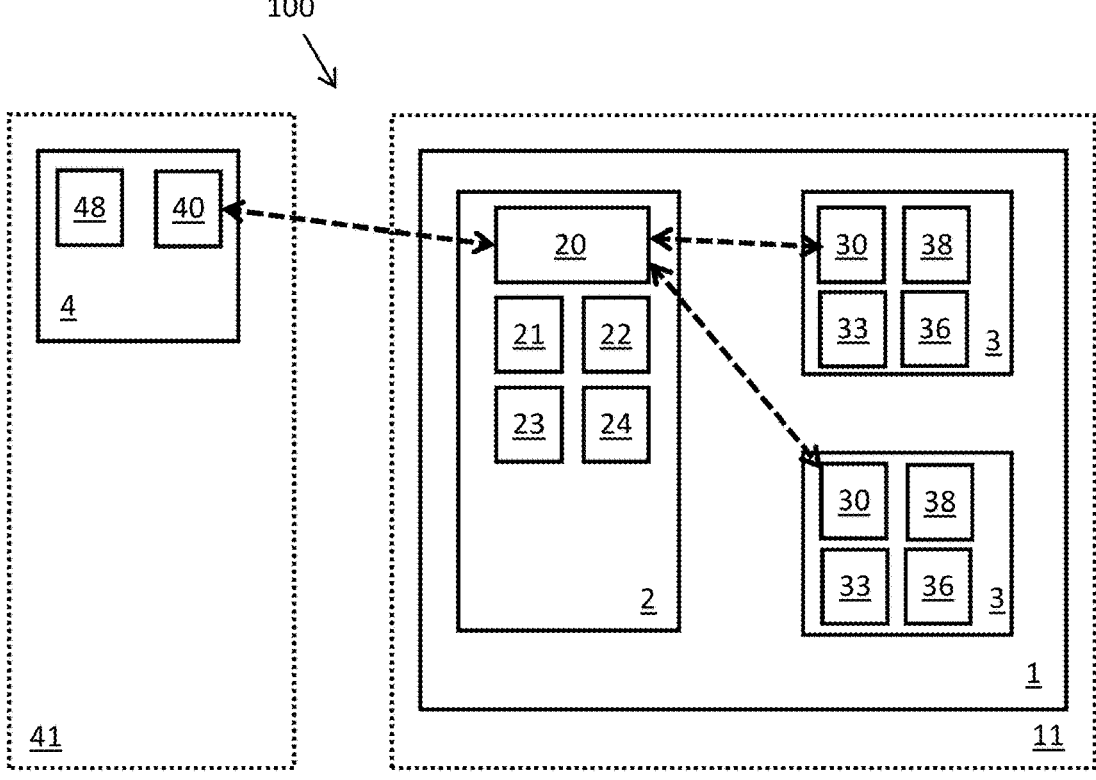
FIG. 9 shows a healthcare system combination deployed in different protected networks.

According to some embodiments, the healthcare system 1 and the integration module 4 are in a shared protected network 11, an example of which is illustrated in FIG. 8. This can e.g. be the case where healthcare system 1 and the integration modules 4 is administrated by a same entity According to some embodiments, the healthcare system 1 is in a first protected network 11 and the integration module 4 is in a second protected network 41, the first protected network 11 being different from the second protected network 41. An example of which is illustrated in FIG. 9. This can e.g. be the case where healthcare system 1 and the integration module 4 is administrated by different entities.

According to some embodiments, the healthcare system combination 100 can comprise two (or more) healthcare systems 1, e.g. a first healthcare system 1 that is in a different protected network as a (specific) integration module 4 and a second healthcare system 1 that is in a same protected network as this (specific) integration module 4.

According to some embodiments, the healthcare system combination 100 can comprise two (or more) integration modules 4, e.g. a first integration modules 4 that is in a different protected network as a (specific) healthcare system 1 and a second integration modules 4 that is in a same protected network as this (specific) healthcare systems 1.

Further proposed is a medical algorithm module 3 designed as one of the two or more medical algorithm modules 3 of the proposed healthcare system 1 resp. proposed the healthcare system combination 100. The medical algorithm modules 3 (e.g. the container images on which they are based) can e.g. be created using specifications of the healthcare system 1, in particular specifications relating to the service application programing interface 20. The medical algorithm modules 3 (e.g. the container images on which they are based) can e.g. be created using a software development kit adapted to the healthcare system 1, in particular adapted to the service application programing interface 20.

Further proposed is a method for operating one of the proposed healthcare systems 1 and/or one of the proposed healthcare system combinations 100, the method comprising the steps of:

receiving, by the service application programing interface 20 (and e.g. from an integration module 4), encrypted medically relevant data MRD and service data SD, the service data SD comprising an indication that a result of a medical algorithm 33 of the healthcare system 1 based on the medically relevant data MRD is ordered, this medical algorithm 33 being the referred to as the ordered medical algorithm 33;

decrypting, by the encryption module 21, the received encrypted medically relevant data MRD;

monitoring, by the security module 22, possible security risks at least for the ordered medical algorithm 33, e.g. by using the received service data SD;

authorizing, by the authorization module 23 and using the received service data SD, the use of the ordered medical algorithm 33 (e.g. by the orderer);

providing, by the service application programing interface 20 to the medical algorithm application programing interface 30 of at least one medical algorithm module 3 comprising the ordered medical algorithm 33, this medical algorithm module 3 being referred to as the chosen medical algorithm module 3, the received medically relevant data MRD;

providing, by the medical algorithm application programing interface 30 of the chosen medical algorithm module 3 to the medical algorithm 33 of the chosen medical algorithm module 3, the received medically relevant data MRD;

algorithmically creating, by the ordered medical algorithm 33 of the chosen medical algorithm module 3 and using the received medically relevant data MRD, a result, this result being referred to as the ordered result;

providing, by the ordered medical algorithm 33 of the chosen medical algorithm module 3 to the medical algorithm application programing interface 30 of the chosen medical algorithm module 3, the ordered result;

providing, by the medical algorithm application programing interface 30 of the chosen medical algorithm module 3 to the service application programing interface 20, the ordered result;

recording, by the activity tracking module 24, at least some activities in the context of the medical algorithms, e.g. at least some activities in the context of the ordered medical algorithm.

The steps of the proposed method are not necessarily processed in the described order, e.g. the monitoring, by the security module 22, of possible security risks at and/or in between multiple steps of the proposed method.

According to some variants, the received service data SD is also encrypted and the method further comprises the step of decrypting, by the encryption module 21, the received encrypted service data SD.

According to some variants, the method further comprises the steps of:

encrypting, by the encryption module 21, the ordered result and—optionally—service data SD, and providing, to an integration module 4, the encrypted ordered result and—optionally—possibly encrypted service data SD (e.g. comprising billing information).

According to some specific variants, the step of monitoring, by the security module 22, possible security risks at least for the ordered medical algorithm 33 comprises controlling, by the security module 22, network traffic, in particular network traffic incoming to the healthcare system 1.

Further proposed are methods embodied by any of the proposed healthcare systems resp. healthcare system combinations.

Further proposed is a computer-readable storage medium comprising instructions which, when executed, causes the computer to carry out one of the proposed methods.

Following up some proposals are disclosed:

1. Proposal

A healthcare system 1 for providing medical insights by receiving medically relevant data (MRD) and providing results of medical algorithms using the medically relevant data (MRD), the medically relevant data (MRD) comprising quantitative medical data created based on at least one diagnostic measurement method, wherein the healthcare system 1 comprises two or more medical algorithm modules 3 and a service module 2;

wherein each medical algorithm module 3 comprises a medical algorithm 33, the medical algorithm 33 being designed for algorithmically creating results using medically relevant data (MRD), is hosted in an isolated runtime environment for its medical algorithm 33, comprises a medical algorithm application programing interface 30, the medical algorithm application programing interface 30 being designed for allowing to receive medically relevant data (MRD) from outside the medical algorithm module 3 and provide the medically relevant data (MRD) to the medical algorithm 33 of the medical algorithm module 3, and to provide results from the medical algorithm 33 to outside of the medical algorithm module 3;

wherein the service module 2 comprises a service application programing interface 20, the service application programing interface 20 being designed for interacting with the medical algorithm application programing interfaces 30 for allowing to provide medically relevant data (MRD) to the medical algorithm modules 3, and to receive results of medical algorithms from the medical algorithm modules 3, the service application programing interface 20 being designed for interacting with one or more integration module(s) 4 for allowing to receive medically relevant data (MRD) from the one or more integration module(s) 4, to provide results of medical algorithms to the one or more integration module(s) 4, and to receive service data (SD) from the one or more integration module(s) 4; and wherein the service module 2 comprises an encryption module 21 designed for decrypting and/or encrypting data, a security module 22 designed for monitoring possible security risks for the medical algorithms 33, an authorization module 23 designed for authorizing, using received service data (SD), the use of at least one of the medical algorithms 33, and an activity tracking module 24 designed for recording at least some activities in the context of the medical algorithms 33.

2. Proposal

The healthcare system 1 of the Proposal 1, wherein the medical algorithms 33 of the two or more medical algorithm modules 3 of the healthcare system 1 are designed for processing quantitative medical data.

3. Proposal

The healthcare system 1 of one of the preceding Proposals, wherein none of the medical algorithm modules 3 comprises an encryption/decryption functionality, a security functionality, an authorization functionality, or an activity tracking functionality.

4. Proposal

The healthcare system 1 of one of the preceding Proposals, wherein each of the medical algorithm modules 3 comprises a medical algorithm graphical user interface 38, the medical algorithm graphical user interface 38 being designed for allowing a user to input medically relevant data (MRD) to the medical algorithm module 3 and to provide the medically relevant data (MRD) to the medical algorithm 33 of the medical algorithm module 3, and to display results from the medical algorithm 33.

5. Proposal

The healthcare system 1 of one of the preceding Proposals, wherein the service module 2 comprises at least one additional service sub-module(s) 25, the at least one additional service sub-module(s) 25 being one or more of the following:

a medical algorithm catalogue database 25a designed for providing information related to the medical algorithms available via the healthcare system 1;

a medical algorithm search module 25b designed for searching the medical algorithms available via the healthcare system 1;

a product labelling information module 25c designed for providing product labelling information on and/or by the respective manufacturer of the medical algorithms available via the healthcare system 1;

a user management module 25d designed for managing user access to the medical algorithms available via the healthcare system 1;

a billing module 25e designed for managing billing information on the use of at least one of the medical algorithms available via the healthcare system 1;

a subscription module 25f designed for managing subscriptions for using at least one of the medical algorithms available via the healthcare system 1;

a usage statistics module 25g designed for providing usage statistics;

a resource management module 25h designed for allocating computing and/or networking resources to the components of the healthcare system 1;

a resource monitoring module 25i designed for monitoring computing and/or networking resources within the healthcare system 1;

a usage prediction module 25j designed for predicting the upcoming usage of medical algorithm modules 3 and for starting and/or terminating medical algorithm modules 3 according to the prediction of the upcoming usage; and a generic input validation module 25k) designed for a generic validation of the medically relevant data (MRD) provided to the healthcare system 1.

6. Proposal

The healthcare system 1 of one of the preceding Proposals, wherein the service module 2 is designed for processing the medically relevant data (MRD) and the results of the medical algorithms without adding medical value to the medically relevant data (MRD) or the results.

7. Proposal

The healthcare system 1 of one of the preceding Proposals, wherein the healthcare system 1 is designed such that the isolated runtime environment of a medical algorithm module 3 cannot directly access the computing and/or network resources of an isolated runtime environment of any other medical algorithm module 3.

8. Proposal

The healthcare system 1 of one of the preceding Proposals, wherein the healthcare system 1 is designed such that the medical algorithm modules 3 can communicate with each other via the service module 2.

9. Proposal

The healthcare system 1 of one of the preceding Proposals, wherein the healthcare system 1 comprises at least one medical algorithm adapter 6 designed for connecting with an external medical algorithm 73 comprised in an external application 7, the medical algorithm adapter 6 comprising an adapter application programing interface 60 designed for allowing to receive medically relevant data (MRD) from the service module 2, to provide medically relevant data (MRD) to the external application 7, to receive results of the external medical algorithm 73 from the external application 7, and to provide results of the external medical algorithm 73 to the service module 2.

10. Proposal

A healthcare system combination 100 of the healthcare system 1 of one of the preceding Proposals and an integration module 4, wherein the integration module 4 comprises an integration module interface 40, 48 designed for providing medically relevant data (MRD) to the healthcare system 1, receiving results of medical algorithms from the healthcare system 1, providing service data (SD) to the healthcare system 1.

11. Proposal

The healthcare system combination 100 of one of the preceding Proposals concerning a healthcare system combination 100, wherein the healthcare system 1 and the integration module 4 are in a shared protected network 11.

12. Proposal

The healthcare system combination 100 of one of the preceding Proposals concerning a healthcare system combination 100, wherein the healthcare system 1 is in a first protected network 11 and the integration module 4 is in a second protected network 41.

13. Proposal

A medical algorithm module 3 designed as one of the two or more medical algorithm modules 3 of the healthcare system 1 resp. the healthcare system combination 100 according to one of the preceding Proposals.

14. Proposal

A method for operating the healthcare system 1 according to one of the preceding Proposals concerning a healthcare system 1, or

of one of the healthcare system combinations 100 of the preceding Proposals concerning a healthcare system combination 100;

the method comprising the steps of:

receiving, by the service application programing interface 20, encrypted medically relevant data (MRD) and service data (SD), the service data (SD) comprising an indication that a result of a medical algorithm 33 of the healthcare system 1 based on the medically relevant data (MRD) is ordered, this medical algorithm 33 being the referred to as the ordered medical algorithm 33;

decrypting, by the encryption module 21, the received encrypted medically relevant data (MRD);

monitoring, by the security module 22, possible security risks at least for the ordered medical algorithm 33;

authorizing, by the authorization module 23 and using the received service data (SD), the use of the ordered medical algorithm 33;

providing, by the service application programing interface 20 to the medical algorithm application programing interface 30 of at least one medical algorithm module 3 comprising the ordered medical algorithm 33, this medical algorithm module 3 being referred to as the chosen medical algorithm module 3, the received medically relevant data (MRD);

providing, by the medical algorithm application programing interface 30 of the chosen medical algorithm module 3 to the medical algorithm 33 of the chosen medical algorithm module 3, the received medically relevant data (MRD);

algorithmically creating, by the ordered medical algorithm 33 of the chosen medical algorithm module 3 and using the received medically relevant data (MRD), a result, this result being referred to as the ordered result;

providing, by the ordered medical algorithm 33 of the chosen medical algorithm module 3 to the medical algorithm application programing interface 30 of the chosen medical algorithm module 3, the ordered result;

providing, by the medical algorithm application programing interface 30 of the chosen medical algorithm module 3 to the service application programing interface 20, the ordered result;

recording, by the activity tracking module 24, at least some activities in the context of the ordered medical algorithm.

15. Proposal

The method of the preceding Proposal for operating the healthcare system 1, the method further comprising the steps of:

encrypting, by the encryption module 21, the ordered result;

providing, to an integration module 4, the encrypted ordered result.

16. Proposal

A healthcare system 1 for providing (medical) insights by receiving input data, in particular medically relevant data (MRD), and providing results of medical algorithms using the input data, the input data comprising quantitative (medical) data, preferably created using at least one diagnostic measurement method, wherein the healthcare system 1 comprises two or more medical algorithm modules 3 and a service module 2;

wherein each (medical) algorithm module 3 comprises a (medical) algorithm 33, the algorithm 33 being designed for algorithmically creating results using input data,

is hosted in an isolated runtime environment for its algorithm 33, comprises a (medical) algorithm application programing interface 30, the algorithm application programing interface 30 being designed for allowing to receive input data from outside the medical algorithm module 3 and provide the medically relevant data (MRD) to the medical algorithm 33 of the algorithm module 3, and to provide results from the algorithm 33 to outside of the algorithm module 3;

wherein the service module 2 comprises a service application programing interface 20, the service application programing interface 20 being designed for interacting with the algorithm application programing interfaces 30 for allowing to provide input data to the algorithm modules 3, and to receive results of algorithms from the algorithm modules 3, the service application programing interface 20 being preferably designed to receive input data from one or more integration module(s) 4, to provide results of algorithms to the one or more integration module(s) 4, and to receive service data (SD) from the one or more integration module(s) 4; and wherein the service module 2 comprises an encryption module 21 designed for decrypting and/or encrypting data, a security module 22 designed for monitoring possible security risks for the algorithms 33, an authorization module 23 designed for authorizing, using received service data (SD), the use of at least one of the algorithms 33, and an activity tracking module 24 designed for recording at least some activities in the context of the algorithms 33.

17. Proposal

The healthcare system 1 of the preceding Proposal, wherein the algorithms 33 of the two or more algorithm modules 3 of the healthcare system 1 are designed for processing quantitative medical data.

18. Proposal

The healthcare system 1 of one of the preceding Proposals, wherein none of the algorithm modules 3 comprises an encryption/decryption functionality, a security functionality, an authorization functionality, or an activity tracking functionality.

19. Proposal

The healthcare system 1 of one of the preceding Proposals, wherein each of the algorithm modules 3 comprises a (medical) algorithm graphical user interface 38, the medical algorithm graphical user interface 38 being designed for allowing a user to input input data to the algorithm module 3 and to provide the input data to the medical algorithm 33 of the medical algorithm module 3, and to display results from the medical algorithm 33.

20. Proposal

The healthcare system 1 of one of the preceding Proposals, wherein the service module 2 comprises at least one additional service sub-module(s) 25, the at least one additional service sub-module(s) 25 being one or more of the following:

a (medical) algorithm catalogue database 25a designed for providing information related to the medical algorithms available via the healthcare system 1;

a (medical) algorithm search module 25b designed for searching the algorithms available via the healthcare system 1;

a product labelling information module 25c designed for providing product labelling information on and/or by the respective manufacturer of the algorithms available via the healthcare system 1;

a user management module 25d designed for managing user access to the algorithms available via the healthcare system 1;

a billing module 25e designed for managing billing information on the use of at least one of the algorithms available via the healthcare system 1;

a subscription module 25f designed for managing subscriptions for using at least one of the algorithms available via the healthcare system 1;

a usage statistics module 25g designed for providing usage statistics;

a resource management module 25h designed for allocating computing and/or networking resources to the components of the healthcare system 1;

a resource monitoring module 25i designed for monitoring computing and/or networking resources within the healthcare system 1;

a usage prediction module 25j designed for predicting the upcoming usage of algorithm modules 3 and for starting and/or terminating algorithm modules 3 according to the prediction of the upcoming usage; and a generic input validation module 25k designed for a generic validation of the input data provided to the healthcare system 1.

21. Proposal

The healthcare system 1 of one of the preceding Proposals, wherein the healthcare system 1 is designed such that the isolated runtime environment of a (medical) algorithm module 3 cannot directly access the computing and/or network resources of an isolated runtime environment of any other (medical) algorithm module 3.

22. Proposal

The healthcare system 1 of one of the preceding Proposals, wherein the healthcare system 1 is designed such that the algorithm modules 3 can communicate with each other via the service module 2.

23. Proposal

The healthcare system 1 of one of the preceding Proposals, wherein the healthcare system 1 comprises at least one (medical) algorithm adapter 6 designed for connecting with an external (medical) algorithm 73 comprised in an external application 7, the medical algorithm adapter 6 comprising an adapter application programing interface 60 designed for allowing to receive input data from the service module 2, to provide input data to the external application 7, to receive results of the external algorithm 73 from the external application 7, and to provide results of the external algorithm 73 to the service module 2.

24. Proposal

A healthcare system combination 100 of the healthcare system 1 of one of the preceding Proposals and an integration module 4, wherein the integration module 4 comprises an integration module interface 40, 48 designed for providing input data to the healthcare system 1, receiving results of algorithms from the healthcare system 1, providing service data (SD) to the healthcare system 1, wherein the service application programing interface 20 being preferably designed to receive input data from the integration module 4, to provide results of algorithms to the integration module 4, and to receive service data (SD) from the integration module 4

25. Proposal

The healthcare system combination 100 of one of the preceding Proposals concerning a healthcare system combination 100, wherein the healthcare system 1 and the integration module 4 are in a shared protected network 11.

26. Proposal

The healthcare system combination 100 of one of the preceding Proposals concerning a healthcare system combination 100, wherein the healthcare system 1 is in a first protected network 11 and the integration module 4 is in a second protected network 41.

27. Proposal

A (medical) algorithm module 3 designed as one of the two or more algorithm modules 3 of the healthcare system 1 resp. the healthcare system combination 100 according to one of the preceding Proposals.

28. Proposal

A method for operating the healthcare system 1 or a healthcare system combination, preferably a healthcare system according to one of the preceding Proposals concerning a healthcare system 1, or one of the healthcare system combinations 100 of the preceding Proposals concerning a healthcare system combination 100, the method comprising the steps of:

receiving, by the service application programing interface 20, encrypted input data and service data (SD), the service data (SD) comprising an indication that a result of an algorithm 33 of the healthcare system 1 based on the input data is ordered, this algorithm 33 being the referred to as the ordered algorithm 33;

decrypting, by the encryption module 21, the received encrypted input data;

monitoring, by the security module 22, possible security risks at least for the ordered algorithm 33;

authorizing, by the authorization module 23 and using the received service data (SD), the use of the ordered algorithm 33;

providing, by the service application programing interface 20 to the algorithm application programing interface 30 of at least one algorithm module 3 comprising the ordered algorithm 33, this algorithm module 3 being referred to as the chosen algorithm module 3, the received input data;

providing, by the algorithm application programing interface 30 of the chosen algorithm module 3 to the algorithm 33 of the chosen algorithm module 3, the received input data;

algorithmically creating, by the ordered algorithm 33 of the chosen algorithm module 3 and using the received input data, a result, this result being referred to as the ordered result;

providing, by the ordered algorithm 33 of the chosen algorithm module 3 to the algorithm application programing interface 30 of the chosen algorithm module 3, the ordered result;

providing, by the algorithm application programing interface 30 of the chosen algorithm module 3 to the service application programing interface 20, the ordered result;

recording, by the activity tracking module 24, at least some activities in the context of the ordered algorithm.

29. Proposal

The method of the preceding Proposal for operating the healthcare system 1, the method further comprising the steps of:

encrypting, by the encryption module 21, the ordered result;

providing, to an integration module 4, the encrypted ordered result.

30. Proposal

A healthcare system 1 for providing results of medical algorithms using at least quantitative medical data created based on at least one diagnostic measurement method, wherein the healthcare system 1 comprises two or more medical algorithm modules 3 and a service module 2;

wherein at least one of the medical algorithm module 3 comprises a medical algorithm 33, the medical algorithm 33 being designed for algorithmically creating results using at least quantitative medical data, is hosted in an isolated runtime environment for its medical algorithm 33, comprises a medical algorithm application programing interface 30, the medical algorithm application programing interface 30 being designed for allowing to receive quantitative medical data from outside the medical algorithm module 3 and provide the quantitative medical data to the medical algorithm 33 of the at least one medical algorithm module 3, and to provide results from the medical algorithm 33 to outside of the at least one medical algorithm module 3;

wherein the service module 2 comprises a service application programing interface 20, the service application programing interface 20 being designed for interacting with the medical algorithm application programing interfaces (30) for allowing to provide quantitative medical data to the at least one medical algorithm module 3, and to receive results of medical algorithm from the at least one medical algorithm module 3, the service application programing interface 20 being designed for interacting with one or more integration module(s) 4 and being designed for allowing:

to receive quantitative medical data from the one or more integration module(s) 4, to provide results of medical algorithms to the one or more integration module(s) 4, and to receive service data (SD) from the one or more integration module(s) 4; and wherein the service module 2 comprises an encryption module 21 designed for decrypting and/or encrypting data, a security module 22 designed for monitoring possible security risks for the medical algorithms 33, an authorization module 23 designed for authorizing, using received service data (SD), the use of at least one of the medical algorithms 33, and an activity tracking module 24 designed for recording at least some activities in the context of the medical algorithms 33.

31. Proposal

The healthcare system 1 of one of the preceding Proposals, wherein none of the medical algorithm modules 3 comprises an encryption/decryption functionality, a security functionality, an authorization functionality, or an activity tracking functionality.

32. Proposal

The healthcare system 1 of one of the preceding Proposals, wherein each of the medical algorithm modules 3 comprises a medical) algorithm graphical user interface 38, the medical algorithm graphical user interface 38 being designed for allowing a user to input at least quantitative medical data to the medical algorithm module 3 and to provide the quantitative medical data to the medical algorithm 33 of the at least one medical algorithm module 3, and to display results from the medical algorithm 33.

33. Proposal

The healthcare system 1 of one of the preceding Proposals, wherein the service module 2 comprises at least one additional service sub-module(s) 25, the at least one additional service sub-module(s) 25 being one or more of the following:

a medical algorithm catalogue database 25a designed for providing information related to the medical algorithms available via the healthcare system 1;

a medical algorithm search module 25b designed for searching the medical algorithms available via the healthcare system 1;

a product labelling information module 25c designed for providing product labelling information on and/or by the respective manufacturer of the medical algorithms available via the healthcare system 1;

a user management module 25d designed for managing user access to the medical algorithms available via the healthcare system 1;

a billing module 25e designed for managing billing information on the use of at least one of the medical algorithms available via the healthcare system 1;

a subscription module 25f designed for managing subscriptions for using at least one of the medical algorithms available via the healthcare system 1;

a usage statistics module 25g designed for providing usage statistics;

a resource management module 25h designed for allocating computing and/or networking resources to the components of the healthcare system 1;

a resource monitoring module 25i designed for monitoring computing and/or networking resources within the healthcare system 1;

a usage prediction module 25j designed for predicting the upcoming usage of medical algorithm modules 3 and for starting and/or terminating medical algorithm modules 3 according to the prediction of the upcoming usage; and a generic input validation module 25k designed for a generic validation of the quantitative medical data provided to the healthcare system 1.

34. Proposal

The healthcare system 1 of one of the preceding Proposals, wherein the healthcare system 1 is designed such that the isolated runtime environment of a medical algorithm module 3 cannot directly access the computing and/or network resources of an isolated runtime environment of any other medical algorithm module 3.

35. Proposal

The healthcare system 1 of one of the preceding Proposals, wherein the healthcare system 1 is designed such that the medical algorithm modules 3 can communicate with each other via the service module 2.

36. Proposal

The healthcare system 1 of one of the preceding Proposals, wherein the healthcare system 1 comprises at least one medical algorithm adapter 6 designed for connecting with an external medical algorithm 73 comprised in an external application 7, the medical algorithm adapter 6 comprising an adapter application programing interface 60 designed for allowing to receive at least quantitative medical data from the service module 2, to provide at least the quantitative medical data to the external application 7, to receive results of the external medical algorithm 73 from the external application 7, and to provide results of the external medical algorithm 73 to the service module 2.

In this text, the terms "according to some embodiments" and "according to some variants" are used, whereby the "some" can mean to reference to embodiments or combinations of embodiments that are mentioned previously or thereafter.

Any of the above discussed embodiments or Proposals can be combined with each other to from new technical workable embodiments.

REFERENCE LIST 1 healthcare system
11 first protected network
100 healthcare system combination
2 service module
20 service application programing interface
21 encryption module
22 security module
23 authorization module
24 activity tracking module
25 additional service sub-modules
3 medical algorithm module
30 medical algorithm application programing interface
33 medical algorithm
35 interface module
36 input validation module
38 medical algorithm graphical user interface
4 integration module
40 integration application programing interface
41 second protected network
48 integration graphical user interface
6 medical algorithm adapter
60 adapter application programing interface
7 external application
70 external application programing interface
71 third second protected network
73 external medical algorithm
9 diagnostic measurement instrument
99 database
100 healthcare system combination
MRD medically relevant data
SD service data

The invention claimed is:

1. A healthcare data processing system comprising:
two or more medical algorithm modules that are programmed with medical algorithms configured to algorithmically generate results based on medical records data (MRD), wherein:
the MRD comprises quantitative medical data from at least one diagnostic measurement,
different medical algorithm modules, that each execute respective medical algorithms of the medical algorithms, are respectively hosted in different isolated runtime environments that execute the respective medical algorithms, and
the different medical algorithm modules comprise medical algorithm application programing interfaces (APIs) configured to receive the MRD and to output the results generated by the respective medical algorithms; and
a service module comprising:
a service API configured to:
receive, from one or more integration modules separate from the service module and the two or more medical algorithm modules, the MRD;
receive, from the one or more integration modules, operational data associated with operation of at least one medical algorithm module of the two or more medical algorithm modules;
provide, via the medical algorithm APIs, the MRD to the at least one medical algorithm module;
receive, via the medical algorithm APIs, the results from the at least one medical algorithm module; and
provide the results to the one or more integration modules;
an encryption module programmed for at least one of decrypting or encrypting data;
a security module programmed for monitoring possible security risks for the medical algorithms;
an authorization module programmed for authorizing, using the operational data, use of at least one of the medical algorithms; and
an activity tracking module programmed for recording at least some activities pertaining to use of the medical algorithms.

2. The healthcare data processing system of claim 1, wherein the medical algorithms, of the two or more medical algorithm modules, are programmed for performing data analytics processing of the quantitative medical data.

3. The healthcare data processing system of claim 1, wherein the two or more medical algorithm modules are restricted from implementing at least one of an encryption functionality, a decryption functionality, a security functionality, an authorization functionality, or an activity tracking functionality.

4. The healthcare data processing system of claim 1, wherein:
each of the two or more medical algorithm modules comprises a medical algorithm graphical user interface, and
the medical algorithm graphical user interface, of a medical algorithm module of the two or more medical algorithm modules, is programmed and configured to:
receive user input of the MRD to the medical algorithm module;
provide the MRD to a respective medical algorithm of the medical algorithm module; and
display results from the respective medical algorithm.

5. The healthcare data processing system of claim 1, wherein:

the service module comprises at least one additional service sub-module, and the at least one additional service sub-module comprises one or more of:

a medical algorithm catalogue database configured to provide information related to the medical algorithms available via the healthcare data processing system;

a medical algorithm search module programmed to search the medical algorithms available via the healthcare data processing system;

a product labelling information module programmed to provide at least one of product labelling information on or by a respective source of the medical algorithms available via the healthcare data processing system;

a user management module programmed to manage user access to the medical algorithms available via the healthcare data processing system;

a billing module programmed to process billing information associated with use of at least one of the medical algorithms available via the healthcare data processing system;

a subscription module programmed to process subscriptions for using the at least one of the medical algorithms available via the healthcare data processing system;

a usage statistics module programmed to track usage statistics associated with usage of the medical algorithms;

a resource management module programmed to allocate at least one of computing resources or networking resources to components of the healthcare data processing system;

a resource monitoring module programmed to monitor the at least one of the computing resources or the networking resources within the healthcare data processing system;

a usage prediction module programmed to predict future usage of the two or more medical algorithm modules and determine optimal selections for at least one of adding or terminating medical algorithm modules according to a prediction of the future usage; or a validation module programmed to validate the MRD provided to the healthcare data processing system.

6. The healthcare data processing system of claim 1, wherein the service module is programmed to process the MRD and the results of the respective medical algorithms without modifying medically relevant information in the MRD or the results.

7. The healthcare data processing system of claim 1, wherein the different isolated runtime environments restrict a first environment wherein a medical algorithm module from accessing at least one of computing resources or network resources associated with a second medical algorithm module.

8. The healthcare data processing system of claim 1, wherein different medical algorithm modules are configured to communicate with each other via the service module.

9. The healthcare data processing system of claim 1, further comprising at least one medical algorithm adapter programmed to connect with an external application including an external medical algorithm, the at least one medical algorithm adapter comprising an adapter API programmed to:

receive the MRD from the service module;

provide the MRD to the external application;

receive, from the external application, external results of applying the external medical algorithm to the MRD; and provide the external results to the service module.

10. The healthcare data processing system of claim 1, wherein an integration module, of the one or more integration modules, comprises an integration module interface programmed and configured to:

transmit the MRD to the service module;

provide the results of processing of the MRD, by the at least one medical algorithm module, to an external application; and provide the operational data to the service module.

11. The healthcare data processing system of claim 10, wherein the healthcare data processing system and the integration module reside within a shared protected network.

12. The healthcare data processing system of claim 10, wherein:

the healthcare data processing system resides within a first protected network, and the integration module resides within in a second protected network different from and connected to the first protected network.

13. One or more non-transitory computer-readable media storing computer-executable instructions associated with a healthcare data processing system that, when executed by one or more processors of a computing system, cause the one or more processors to:

execute different medical algorithm modules within different respective isolated runtime environments, wherein:

the different medical algorithm modules are configured to use respective medical algorithms to process medical records data (MRD);

receive, via a service application programming interface (API) of a service module separate from the different medical algorithm modules, the MRD from at least one integration module;

provide, via the service API of the service module, the MRD to at least one medical algorithm module of the different medical algorithm modules;

transmit, via the service API of the service module, and to the at least one integration module, results generated by the respective medical algorithms of the at least one medical algorithm module based on the MRD.

14. A computer-implemented method for processing healthcare data, the computer-implemented method comprising:

receiving, by a service module, from at least one integration module, and via a service application programming interface (API), medical records data (MRD);

receiving, by the service module, from the at least one integration module, and via the service API, operational data associated with operation of at least one of a plurality of medical algorithm modules;

transmitting, by the service module, and via the service API, the MRD to the at least one of the plurality of medical algorithm modules, wherein different medical algorithm modules of the plurality of medical algorithm modules:

are programmed to respectively operate in different isolated runtime environments;

are programmed with a respective medical algorithms that are programmed to algorithmically generate results based on the MRD; and comprise a medical algorithm API programmed to:

receive the MRD;

provide the MRD to the respective medical algorithms; and transmit the results generated by the respective medical algorithms;

receiving, by the service module, and via the service API, the results of the respective medical algorithms from the at least one of the plurality of medical algorithm modules; and, providing, by the service module, and via the service API, the results to the at least one integration module, wherein the service module comprises:

an encryption module programmed for at least one of decrypting or encrypting data;

a security module programmed for monitoring possible security risks for the respective medical algorithms;

an authorization module programmed for authorizing, using the operational data, use of the at least one of the plurality of medical algorithm modules; and an activity tracking module programmed for recording at least some activities pertaining to use of the respective medical algorithms.

15. The computer-implemented method of claim 14, further comprising:

receiving, by the service module, and via the service API, encrypted MRD;

accessing, using the encryption module, the MRD by decrypting the encrypted MRD;

identifying, by the service module, and based on the operational data, a request to process the MRD with the at least one of the plurality of medical algorithm modules;

monitoring, by the security module, the possible security risks associated with the at least one of the plurality of medical algorithm modules indicated by the request;

authorizing, by the authorization module, and using the operational data, the use of the at least one of the plurality of medical algorithm modules indicated by the request;

providing, via the service API, to the medical algorithm API of the at least one of the plurality of medical algorithm modules indicated by the request, the MRD;

receiving, via the service API, the results of the respective medical algorithms of the at least one of the plurality of medical algorithms based on the MRD; and recording, by the activity tracking module, the at least some activities relating to the use of the at least one of the plurality of medical algorithm modules indicated by the request.

16. The computer-implemented method of claim 15, further comprising:

generating, by the encryption module, encrypted results by encrypting the results; and providing, via the service API, and to the at least one integration module, the encrypted results.

17. The healthcare data processing system of claim 1, wherein the different isolated runtime environments comprise at least one of different containers or different virtual machines.

18. The healthcare data processing system of claim 7, wherein the different isolated runtime environments cause at least one of global variables or other data associated with operations of the second medical algorithm module to be inaccessible by the first medical algorithm module.

19. The healthcare data processing system of claim 7, wherein:

the first medical algorithm module is configured to use a first medical algorithm to process the MRD, the second medical algorithm module is configured to use a second medical algorithm to process the MRD, and the second algorithm is:

different from the first algorithm, or a second instance of the first algorithm.

20. The one or more non-transitory computer-readable media of claim 13, wherein the computer-executable instructions cause the one or more processors to instantiate the different medical algorithm modules in different containers, associated with the different respective isolated runtime environments, based on one or more corresponding predefined container images.

* * * * *